(12) United States Patent
Dykstra et al.

(10) Patent No.: US 6,613,164 B2
(45) Date of Patent: *Sep. 2, 2003

(54) METHOD OF FORMING A TUBULAR BLANK INTO A STRUCTURAL COMPONENT AND DIE THEREFOR

(75) Inventors: William C. Dykstra, Rockford, MI (US); George D. Pfaffmann, Farmington Hills, MI (US); Xin Nmn Wu, Detroit, MI (US)

(73) Assignee: Hot Metal Gas Forming Intellectual Property, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/944,769

(22) Filed: Sep. 4, 2001

(65) Prior Publication Data

US 2002/0003011 A1 Jan. 10, 2002

Related U.S. Application Data

(63) Continuation of application No. 09/481,376, filed on Jan. 11, 2000, now Pat. No. 6,322,645.
(60) Provisional application No. 60/155,969, filed on Sep. 24, 1999.

(51) Int. Cl.$^7$ ............................................. B21D 26/02
(52) U.S. Cl. .................. 148/520; 148/570; 148/571; 72/62; 72/342.96
(58) Field of Search ............................ 148/520, 570, 148/571; 72/62, 342.96

(56) References Cited

U.S. PATENT DOCUMENTS

| | | | |
|---|---|---|---|
| 4,584,860 A | 4/1986 | Leonard | |
| 4,637,844 A | 1/1987 | Pfaffmann | |
| 5,410,132 A | 4/1995 | Gregg et al. | |
| 5,530,227 A | 6/1996 | Matsen et al. | |
| 5,868,023 A | 2/1999 | Wehner et al. | |
| 5,960,658 A | 10/1999 | Hudson et al. | |
| 5,992,197 A | 11/1999 | Freeman et al. | |
| 6,067,831 A | 5/2000 | Amborn et al. | |
| 6,151,940 A | 11/2000 | Amborn et al. | |
| 6,322,645 B1 * | 11/2001 | Dykstra et al. | 148/520 |
| 6,349,583 B1 * | 2/2002 | Kleinschmidt et al. | 72/62 |
| 6,401,509 B1 | 6/2002 | Amborn | |
| 6,460,250 B1 | 10/2002 | Anborn et al. | |

FOREIGN PATENT DOCUMENTS

GB 2 330 104 A 4/1999

OTHER PUBLICATIONS

Hot Metal Gas Forming (HMGF) by Auto Body Consortium, Inc. Mar. 18, 1998, NIST Advanced Technology, Program General Program Competition 98–01.

* cited by examiner

Primary Examiner—George Wyszomierski
(74) Attorney, Agent, or Firm—Fay, Sharpe, Fagan, Minnich & McKee

(57) ABSTRACT

A method of forming an elongated tubular blank into a tubular structural component having a predetermined outer configuration, the method comprising: providing a shape imparting shell formed from a low permeability, rigid material which includes an inner surface defining the predetermined shape, plugging the open ends of the tubular blank, placing the plugged blank into the shell, and forming the tubular blank into the tubular component by inductively heating axial portions of the blank by axially spaced conductors adjacent the shell while or before forcing gas at a high pressure into the plugged blank until the blank conforms to at least a portion of the inner surface of the shell to form the structural component.

131 Claims, 16 Drawing Sheets

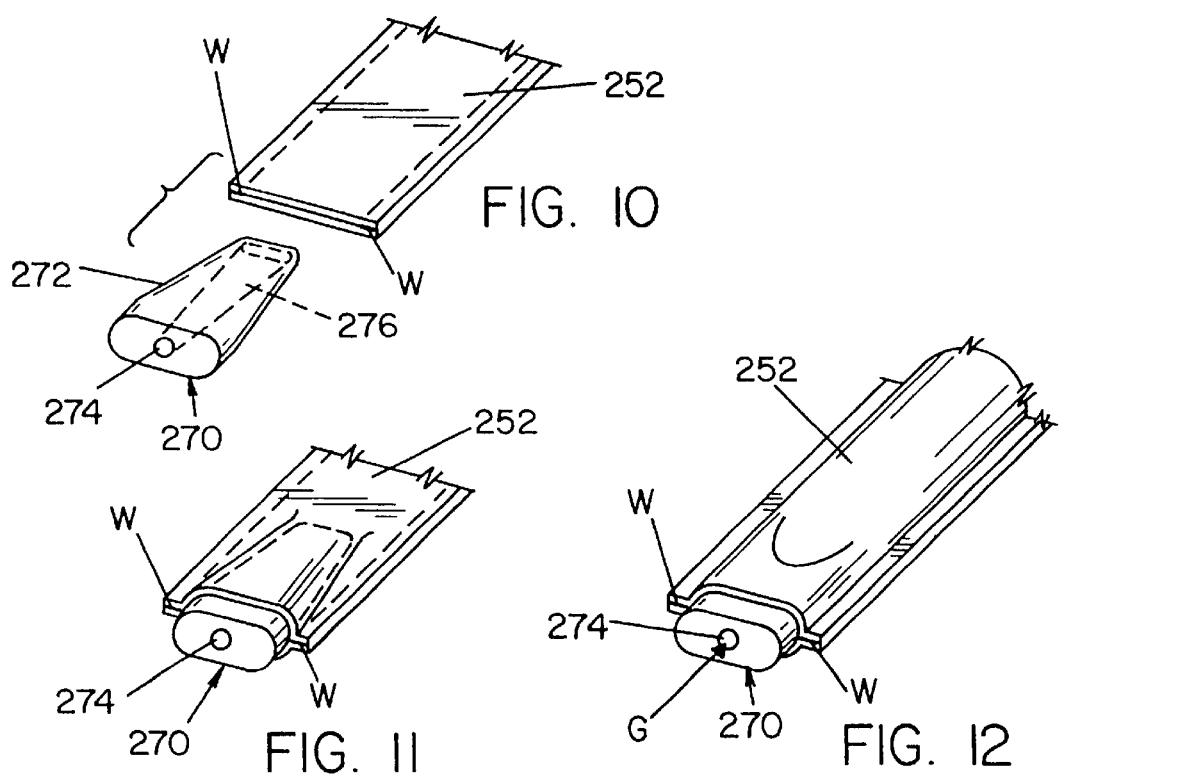
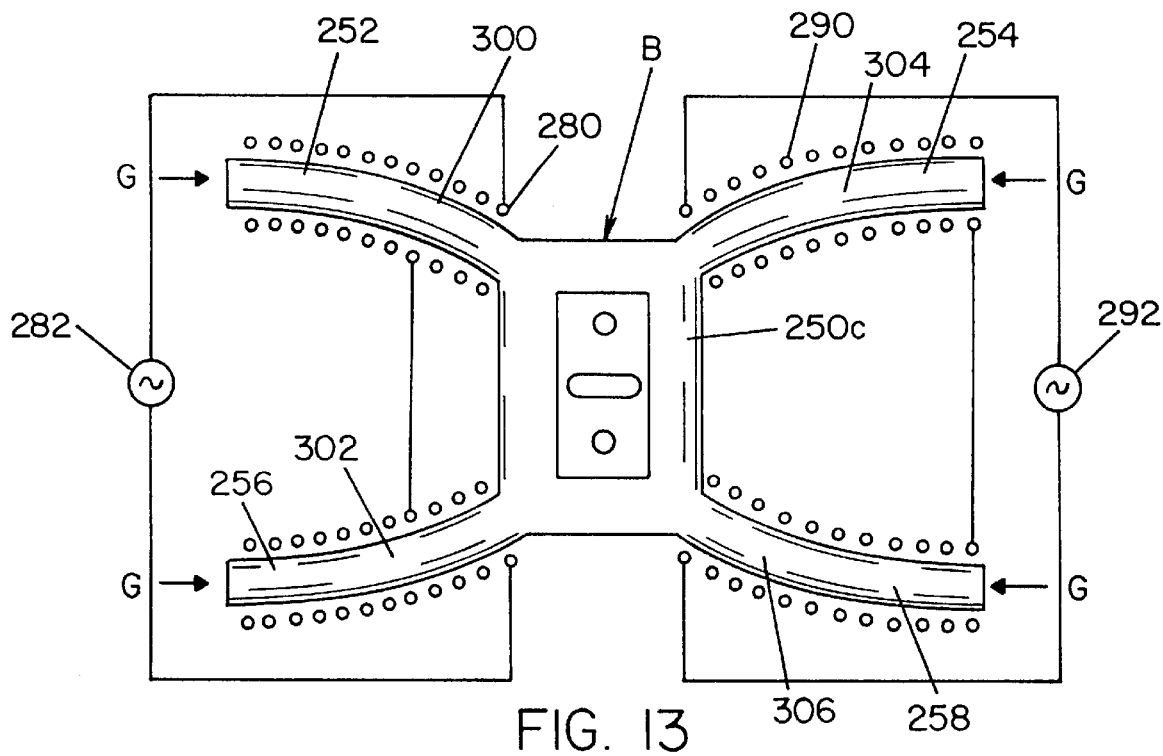

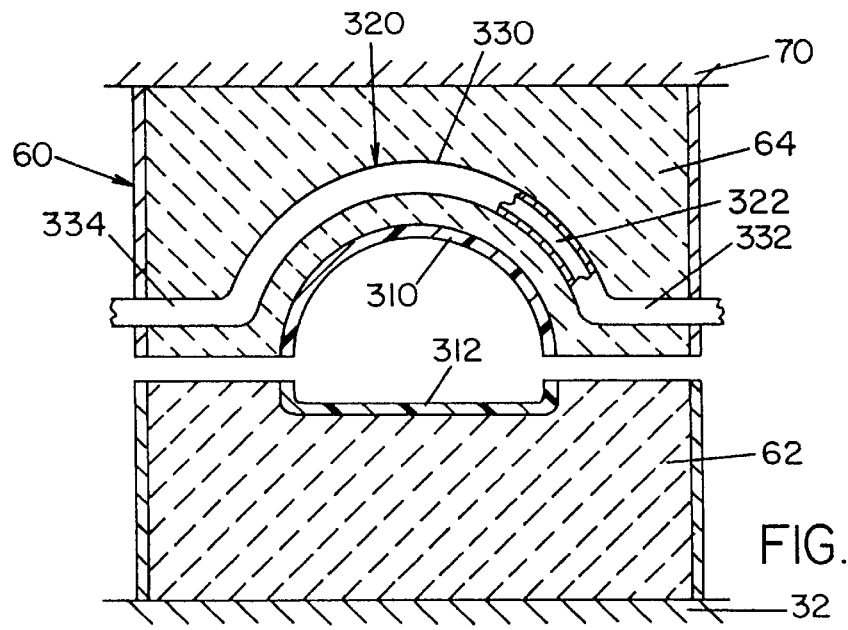
FIG. 14
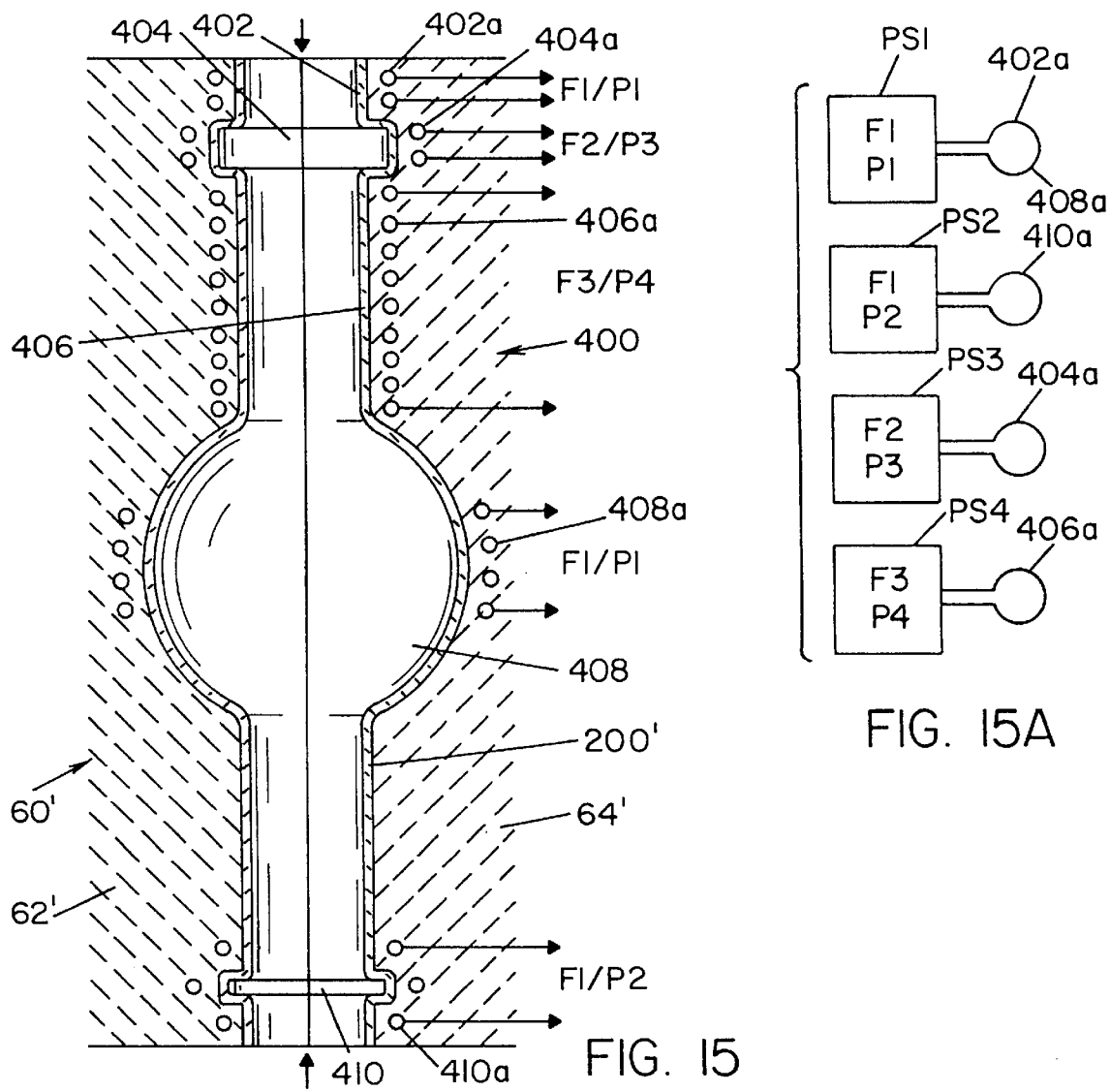
FIG. 15
FIG. 15A

METHOD OF FORMING A TUBULAR BLANK INTO A STRUCTURAL COMPONENT AND DIE THEREFOR

This patent application is a continuation of Ser. No. 09/481,376 filed on Jan. 11, 2000, now U.S. Pat. No. 6,322,645, which in turn claims the benefit of provisional application No. 60/155,969 filed Sep. 24, 1999, now abandoned, and incorporated herein by reference.

The present invention relates to the art of forming structural components such as used in motor vehicles and more particularly to a method of forming a tubular blank into a structural component by use of high pressure inert gas.

INCORPORATION BY REFERENCE

The invention involves formation of tubular metal components of structural type as used in automotive support frame where a tubular blank is formed to match the shape defined by the inner surface of a shell or cavity. In accordance with the invention, the shell or cavity is in a low permeability cast support structure wherein induction heating coils are embedded for inductively heating the tubular blank preparatory to formation into the desired shape imparted by the shell or cavity. A similar technology has been developed by Boeing Company wherein a flat plate is formed against a contoured wall by gas pressure. This process is referred to as superplastic forming of the plate and is disclosed in Gregg U.S. Pat. No. 5,410,132, incorporated by reference herein. This patent illustrates a process whereby the temperature of the metal plate is increased to a superplastic temperature by induction heating conductors mounted in a ceramic, low permeability cast die surrounding the metal forming chamber defined between two dies. This gas pressure chamber includes one surface against which the plate is formed. The Boeing process, as disclosed in Gregg U.S. Pat. No. 5,410,132, utilizes induction heating coils for the purposes of heating the metal preparatory to forming against a shaped surface by using high pressure gas on one side of the plate. The extent to which the Boeing patent defines a ceramic die with embedded induction heating coils and the use of a high pressure inert gas for forming the metal sheet, the technology relates to the technology employed in the present invention. For that reason, details of the die induction heating coils and high pressure gas forming may not be repeated to understand the present invention. In Matsen U.S. Pat. No. 5,530,227, Boeing Company further illustrates more details about the die, induction heating coils in a cast die forming material and the dies used by Boeing Company for superplastic forming of a sheet metal plate. Matsen U.S. Pat. No. 5,530,227 is also incorporated by reference herein so that the details of the technology developed by Boeing Company and usable in the present invention need not be repeated. Hot metal gas forming of steel is generally described in a joint venture proposal to the National Institute of Standards and Technology on Mar. 18, 1998. The proposal is incorporated by reference herein as background information.

BACKGROUND OF INVENTION

The present invention is primarily directed toward the production of structural components of the type used in the automotive field and it will be described with particular reference thereto; however, the invention is much broader and may be used for forming various structural components from tubular sheet metal blanks. In the past, such structural components were normally produced by stamping, forming and welding. In an effort to obtain complex shapes, such components have been formed by a hydroforming process wherein tubular blanks are provided from sheet steel material having specific initial strength and elongation. The tubular blank is cut to length and pre-bent or preformed into a shape approximating the shape of the finished structural component. The preformed tubular element is loaded into a two piece die closed in a hydraulic press typically having a closing pressure between about 3500–8000 tons. The exposed ends of the tubular blank are sealed and the tube is filled with a water and oil mixture. The internal pressure of the water and oil mixture is raised to a high level in the general neighborhood of 20,000–80,000 psi which pressurized liquid expands the tubular blank into the shape of a steel die cavity machine in two die members of a die set carried by the hydraulic press. The cavities of the two die members have the desired final shape for the structural component so that as the tubular blank is expanded into the cavity, the outer shape of the component captures the shape of the cavity. This process produces a relatively accurate complex outer shape for the structural component. To relieve the fluid pressure, holes are pierced into the formed structural component. Thereafter, the two die members are opened by the hydraulic press and the liquid is drained from the formed structural component. Secondary machinery operations, such as trimming and cutting mounting holes, is then performed to produce a desired component for final assembly. This process is gaining popularity because it forms the component from the inside so complex shapes are possible; however, the total cycle time for hydroforming is at least about 25–45 seconds. The equipment to direct high pressure liquid into the tubular blank is extremely large and expensive. In addition, the die members are expensive machined parts and have a short life. Hydroforming operations have a general limitation that they are used primarily for bending of the tubular blank, since the steel being formed is processed at ambient temperature which limits the maximum strain rate for the metal being formed. Pressure of the liquid used in the hydroforming must be extremely high to deform the relatively cold sheet metal of the tubular blank into simple configurations. Consequently, hydroforming is used primarily for bending and straightening tubular elements into the desired final shape. Even though there are process limitations in using hydroforming to make tubular structural components, a substantial technology field has developed around this process. In a feature of hydroforming, the sheet steel tubular blank is formed into desired shapes while additional material is forced axially into the die cavity so the wall thickness does not drastically decrease as the volume of a given cross section increases during the processing by high pressure liquid.

Hydroforming is the primary prior art constituting the background of the present invention. However, blow forming of plastic sheets has been used for years to produce high volume plastic containers using conventional steel die members. Of course, such die members used in plastic blow forming can not be used for forming steel. For that reason, hydroforming is used for metal, instead of blow forming as used in the plastics industry. The highly developed technology of hydroforming of steel tubes and blow forming of plastic sheets are background of the present invention, but are not economically usable for forming sheet steel tubular blanks into tubular structural components. In addition, these prior processes do not have the capability of controlling the metallurgical characteristics along the length of the tubular blank, as obtainable by the present invention.

Even though hydroforming of sheet steel and blow forming of plastic sheets are the basic background to the present invention, it has been found that certain features of the technology disclosed by Boeing Company for superplastic forming sheet metal plates by high pressure gas are used in practicing the invention. The Boeing Company process is not background information from the standpoint that it is not capable of forming a tubular metal blank into a structural tubular component and is not capable of controlling the metallurgical characteristics of the metal forming the structural tubular component. These are all advantages of the present invention.

SUMMARY OF INVENTION

The present invention provides a completely different type of technology which is dissimilar to hydroforming of steel and blow forming of plastic sheets. In accordance with the present invention, a tube is made from sheet metal formed by controlled rolling of the sheet. The sheet metal is formed into a tubular blank which is preheated using resistance electric heating and preformed to the desired axial profile. The preheated blank is placed into the shell or cavity of a specially constructed die set in which are embedded induction heating conductors or coils spaced axially along the cavity. The tubular blank has an open end or open ends which are plugged or sealed. The tubular blank is expanded by high inert gas at a pressure in the general range of 100–5,000 psi, but preferably in the range of 200–1000 psi. During expansion, the induction heating conductors or coils induce an A.C. voltage into the metal of the blank which cause $I^2R$ heating of the blank. Consequently, the blank can be rapidly expanded. The cavity or shell having the desired predetermined shape surrounds the expanding tube to impart, to the outer surface of the blank the shape of the shell or cavity. The structural element is then cooled at a controlled quenching rate to control the metallurgical characteristics to enhance the mechanical properties of the resulting structural components.

By using the present invention there is developed a new metal forming process technology that reduces the cost to process tubular structural components by at least 50% and reduces the time to build, and the cost to build, the forming die members by at least about 40%. By using structural components formed by the unique process of the present invention, the structural component is reduced in weight by approximately 20%. Although the inventive method involves the use of gas to expand the sheet metal tubular blank into the desired configuration for the structural element, the invention actually involves substantial improvements in this general process. In other words, the present invention is not merely the use of high pressure inert gas as a substitute for high pressure liquid used in hydroforming. One aspect of the invention involves the formation of a unique cavity or shell which is mounted in the die members of the die set opened and closed by the hydraulic press. The shells and die members are constructed so that the tubular blank being formed into the shape of the shell or cavity can be heated inductively along its length to control the heat of the tubular blank before and during the forming process. This can not be done in hydroforming. By using induction heating in the tools or die members, the heating conductors or coils can localize the heating along the length of the blank. The die set not only supports induction heating conductors, but also (a) supports the forces necessary to restrain the tubular blank being formed and (b) provides increased wear resistance. By using the present invention, the yield strength along the length of the resulting component or end product is varied by proper heating and cooling. This is particularly advantageous if extended deformation is required in producing the desired finished shape of the structural element.

By using the present invention, a tubular structural component can be formed having more detailed outer configurations than obtainable with hydroforming. Indeed, the invention obtains the result generally associated with blow forming plastic sheets, but for sheet metal components. This is accomplished by utilizing a unique and novel material from which the die member containing the forming cavity is constructed so induction heating along the length of the tubular blank can be varied. Consequently, the material utilized for the shape defining cavity or shell has low permeability and is rigid. It is supported in a cast low permeability material holding the forming cavity in two die members movable together by a hydraulic press. By making this type of die member, induction heating along the tubular blank can be varied so that subsequent cooling of specific portions of the structural component provides desired metallurgical characteristics. The end product does not need to have a uniform metallurgical characteristic associated with the total processing operation which is the result of the Boeing process. Such process uniformly heats the sheet and does not quench harden the sheet.

In accordance with the present invention there is provided a method of forming an elongated tubular metal blank into a tubular structural component having a predetermined outer configuration, wherein the method uses a shape imparting shell formed from a low permeability, rigid material. The shell is in the form of a first and second half shell each of which includes an inner surface defining the predetermined shape of the final structural component. The half shells have laterally spaced edges which define a parting plane between the two half shells when the half shells are brought together. The half shells form a total shell or cavity having an inner surface defining the shape to be imparted to the structural component as the blank is expanded into the cavity. One half shell is mounted in one die member and the other half shell is mounted in the other die member so the die set can be opened and closed to define the part forming cavity. By employing a rigid, hard material defining the shape to be imparted to the final part, the shell can be supported as a separate element in a cast non-magnetic material held in the framework of the dies. By utilizing a cast material, together with an inner shell or cavity engaging the workpiece itself, the properties of the shell are not dictated by the compressive force carrying capacity necessary for the cast material. Consequently, by using a cast material which is different from the rigid, hard material actually engaging the tubular member during the forming process, both of these materials can be optimized. Since the invention utilizes induction heating surrounding the shell, the material of the shell and the material supporting the shell are both low permeability to be generally transparent to the magnetic fields created by the conductors embedded in the cast material. To expand the blank, the open ends of the tubular blank are plugged while in one of the half shells in one of the die members. The other half shell is then positioned over the blank and held in position by pressure in the general range of 50–500 tons. Thereafter, the tubular blank is formed into the final shape by inductively heating axial portions of the blank. When spaced portions are heated axially spaced conductors adjacent the shell or cavity are used. The heating is done while the tubular blank is forced into the cavity to create the desired shape. Consequently, tube expansion is accompanied by forcing an inert gas, such as nitrogen or argon, at high pressure into the plugged blank until the blank conforms to at least a portion of the inner surface of the first and second half shells defining the shape cavity during and/or after the tube is inductively heated. By utilizing conductors spaced axially along the workpiece and embedded in the cast material around the shell, the metal of the blank is inductively heated to facilitate the forming operation caused by the expansion action of the internal gas pressure. By using the present invention, the total length of the tubular blank can be heated inductively and/or selected portions can be heated inductively. In practice, induction heating is normally accomplished to a greater extent where the primary formation or elongation is to be accomplished in practicing the invention. In this aspect of the invention, there is provided a unique formation two component die member. The inner component defines the shape and the outer component defines the compressive force absorbing mass. Thus, the two components of the member can be optimized. A better shape can be imparted to the workpiece and an inexpensive compressive force absorbing cast material can be used. This cast material is employed for embedding the induction heating conductors that inductively heat of the tubular blank during forming or prior to forming. Indeed, the induction heating can be before and/or during the gas forming operation.

In accordance with this aspect of the invention, the high hardness rigid material or shell is ceramic and preferably fused silicon. It is also possible to select material from the class consisting of silicon nitride, silicon carbide, beryllium oxide, boron oxide and zirconium. In the preferred embodiment the shell has a thickness of $3/8$–$5/8$ inches and is cast from silicon nitride with or without sintering. Then a hard cutting tool type ceramic may be coated on the shaped surface. In another process for making the rigid hard shell, powder silica is compressed to 50%–70% and then the shape is machined into the block. Vacuum removes the air while nitrogen is used to penetrate. This gives a silicon nitride shell. It may be a block supported in the die member or a thin walled shell. As can be seen, the ceramic material used to construct the shape imparting shell is different than the inexpensive ceramic material forming the remainder of the die member, which material is merely a compressive force resistant material supported in a metal framework. The shell may be coated.

It is possible to select materials, such as oxides, i.e. refractory cements, glass ceramics, high strength ceramics (e.g. silicon nitride, silicon carbide, zirconium oxide etc.). These materials can be either monolithic, or with various forms of reinforcements (composites), such as ceramic particulate reinforced glass. As an example, in one process for making the rigid hard shell, powder silica is merely compressed by more than 60% of full density. In one process, a silica-based glass ceramic is melted, mixed with silicon carbide reinforcement and cast into the desired shell shape.

In accordance with another aspect of the present invention, the predetermined shape has an axial profile which may undulate. Thus, the final part may have curves and bends. It is within an aspect of the invention to preform tubular blank into this axial profile so the blank generally corresponds to the profile of the final part.

In accordance with another aspect of the invention, the tubular blank is resistance heated by passing an alternating current, or direct current, through the sheet metal of the blank preparatory to moving the hollow or tubular blank into the forming shell. Induction preheating is also used. Consequently, the total tubular blank is at an elevated temperature so that the induction heating of the blank merely raises the temperature beyond the preheated temperature of the blank.

In accordance with another aspect of the present invention, the induction heating is varied along the length of the tubular blank or over the locations of the flat hollow blanks whereby different locations are inductively heated to different temperatures, at different time intervals, to achieve optimal strain distribution control. Indeed, axial portions of the workpiece are inductively heated in different induction heating cycles dictated by the desired metallurgical characteristics and deformation amount at axial portions of the tubular blank. By changing the induction heating effect along the blank preparatory to forming, or during forming, the induction heating process is "tuned" with temperatures at different locations on the tubular blank. In this manner, the desired metallurgical characteristics and/or the optimum forming procedure is obtainable. The use of induction heating in this manner to selectively process portions of the tubular sheet metal blank distinguishes the present invention from any prior forming processes.

The use of induction heating to different degrees at various portions of the tubular blank allows thermal processing of the various portions differently. Variations in the induction heating along the length of the blank can be accomplished by a number of coils or conductors along the forming cavity. The heating cycle of selected portions is controlled by varying the frequency, the power, the distance of the conductors from the workpiece, the spacing between axially adjacent conductors and the induction heating cycle time. By changing one or more of these induction heating parameters, the tubular blank being formed has controlled heating along its length. The temperature is controlled. For steel, it is generally 1400° F. to 1800° F. Aluminum is heated to a lower temperature. The objective is to produce a specific temperature that creates the proper formability plasticity.

In accordance with another aspect of the present invention, the heated, formed tubular structural component is transferred into a quench station. In the quench station, the previously inductively heated structural component is liquid and/or air quenched along its length. In accordance with another aspect of the invention, the quenching action is also "tuned" along the length of the workpiece. By controlling the amount of heating during the forming process and the quenching time, flow rate and/or temperature of the liquid, metallurgical properties of the steel or aluminum forming the structural component is controlled at various portions along the length. By practicing the present invention, the tubular blank is inductively heated in a controlled fashion at various locations along the length of the blank. The resulting tubular structural component is then quenched in a controlled fashion to dictate the metallurgical characteristics along the various portions along the length of the structural component.

In accordance with a more limited aspect of the present invention, as the tubular blank is expanded into the shape of the shell or cavity carried by the two spaced die members, portions of the tubular workpiece outside of the die members is pushed into the cavity or shell to provide additional metal to prevent drastic reduction in the wall thickness when substantial expansion of the tubular blank is dictated by the desired final shape of the structural component. This procedure is a concept used in hydroforming of steel tubular blanks. In accordance with still a further aspect of the invention, the pressure of the forming inert gas within the tubular blank is sensed and controlled at the desired pressure. The gas pressure is controlled in the general range of 200–1000 psi which is sufficient to expand the inductively heated workpiece by using the method of the present invention. The gas pressure is controlled either by controlling the pressure introduced into the plugged tubular blank or, in the alternative, by venting the pressure from the blank.

In accordance with still a further aspect of the present invention, there is provided a die set for forming an elongated tubular steel blank into a tubular structural component. This die set comprises a shape imparting shell formed from a low permeability, rigid material. The shell has a thickness of ⅜–⅝ inches and is preferably formed from cast silicon nitride which is a hard cutting tool type ceramic. In practice, a non-sintered silicon nitride shell has a thin coating on the inner shaped surface of the shell formed by sputter deposed dense silicon nitride. Coatings of silicon carbide and titanium nitride have also been used. The hard shell is in the form of first and second half shells each of which includes an inner surface (preferably a coated surface) defining the predetermined shape, an outer support and mounting surface and spaced lateral edges which edges define the parting plane between the two half shells when the half shells are brought together. The halves form a total shell into which the tubular blank is expanded. The first die member has an upper side and a lower side and a non-magnetic support framework for carrying the first half shell mounted in the metal framework by a cast compressive force transmitting non-magnetic fill material. This fill material is preferably fused silica. The lateral spaced edges of the first half shell facing outwardly from the lower side of the first die member. In a like manner, the second die member has an upper side and a lower side and a non-magnetic support frame for carrying the second half shell mounted in the framework by a cast compression force transmitting non-magnetic fill material. The fill material is preferably fused silica. The laterally spaced edges of the second half shell facing outwardly from the upper side of the second die member. The first and second die members are moved together to capture the blank in the shape imparted shells formed by the hard, rigid shell halves. The two die members carry a shell formed from a hard, rigid material selected for the purposes of long die wear. The shell material is selected to maintain the desired shape of the shell for long periods of time. By using this type of die set, the induction heating conductors or coils are embedded within the cast fill material surrounding the shape imparting inner surface of the hard, rigid shell.

In accordance with another aspect of the present invention there is provided a method of forming an elongated tubular blank into a tubular component having a predetermined outer configuration. This method comprises plugging the open end or ends of the tubular blank, placing the plugged blank into a shell or cavity with an inner surface surrounding the blank and having a predetermined outer configuration, forming the tubular blank into the component by inductively heating along the length of the blank by axially spaced conductors surrounding the cavity, while forcing inert gas at a high pressure into the plugged blank until the blank conforms to at least a portion of the inner surface of the cavity or shell to form the desired final component. The inert gas is nitrogen or argon. The shell has a thickness in the general range of ⅜–⅝ inches and the metal being formed is steel and aluminum.

In accordance with still a further aspect of the invention, an elongated tubular blank is formed into a tubular component having a predetermined outer configuration. This method involves plugging the open ends of the tubular blank, placing the plugged blank into a shell or cavity with an inner surface surrounding the blank and having a predetermined shape, forming the tubular blank into the component by inductively heating axial portions along the length of the blank while forcing gas at high pressure into the blank until the blank conforms to at least a portion of the inner surface of a cavity and transferring the formed component to a quench station where the component is selectively quenched along its axial length.

The induction heating used in the present invention is varied along axial portions of the tubular blank and the quenching is also controlled along the axial length of the blank. In this manner, the forming operation is optimized and the metallurgical properties of the resulting structural component are optimized. Since the invention is a hot forming process, it provides a means to significantly improve material formability. Within the acceptable forming time (i.e. 15 seconds), or deformable speed (strain rate greater than 0.1 per second), the process achieves more than 100% uniform tensile elongation for several aluminum alloys, as compared to about 30% in cold forming processes. The hot metal gas forming provides enhanced formability, thus greatly enhances manufacturability of structural parts and offers increased design flexibility. Consequently, the process part has reduced weight, tooling costs and development time.

The primary object of the present invention is the provision of a method of forming a tubular metal blank into a tubular structural component, with the desired outer shape, which method controls the heating and metallurgical characteristics by controlled induction heating and controlled quenching.

A further object of the present invention is the provision of a method, as defined above, which method overcomes the disadvantages of hydroforming such as limited shapes, low die life and high equipment costs.

Still a further object of the present invention is the provision of a method, as defined above, which method has reduced the tooling cost, reduced process cycle time, and increased design flexibility.

Yet another object of the present invention is the provision of a method, as defined above, which method allows size or shape changes substantially over 10% of the original tube diameter without requiring secondary operations or material annealing operations between processing.

Still a further object of the present invention is the provision of a die set for practicing the method as defined above, which die set includes a shell or cavity formed from a hard, rigid ceramic supported by a non-magnetic cast fill material so the shell has long life and the fill material has high compressive force characteristics.

Another object of the present invention is the provision of a method, as defined above, which method involves expanding a tubular workpiece heated inductively by controlled heating cycles. Then selectively quenching the workpiece is used to control the metallurgical properties of the finished product using rapid quenching, arrested cooling or combinations thereof.

These and other objects and advantages will become apparent from the following description taken together with the accompanying drawing.

BRIEF DESCRIPTION OF DRAWING

FIGS. 10 and 11 are pictorial views showing the operation of plugging one of the open ends of a leg of the tubular blank shown in FIGS. 8 and 9;

FIG. 12 is a pictorial view similar to FIGS. 10 and 11 illustrating the plugged end of a tubular blank as it is being formed by air pressure introduced through the plug;

FIG. 13 is a top plan view of the tubular blank shown in FIGS. 7–12 as it is being formed by pressurized gas while being selectively induction heated;

FIG. 14 is a cross sectional view of the two die members used in practicing the present invention with a differently shaped part where the induction heating coils or conductors are positioned along only one side of the die member;

FIG. 15 is a cross sectional view of the two die members used in practicing the present invention for producing a particularly tubular structural component with a different expanded shape and illustrating the distribution of induction heating coils along the length of the cavity for forming the tubular blank;

FIG. 15A is a schematic block diagram showing power supplies to develop the induction heating parameters used in the conductors or heating coils shown in FIG. 15;

PREFERRED EMBODIMENTS

Figure 1:
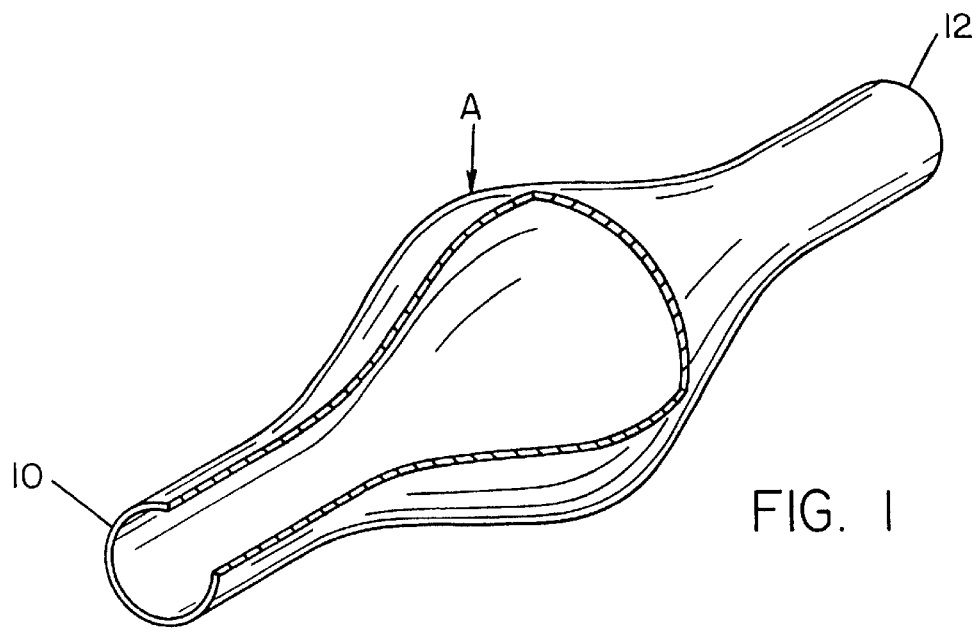
FIG. 1 is a pictorial view of a representative tubular structural component formed by use of the present invention.
Figure 4:
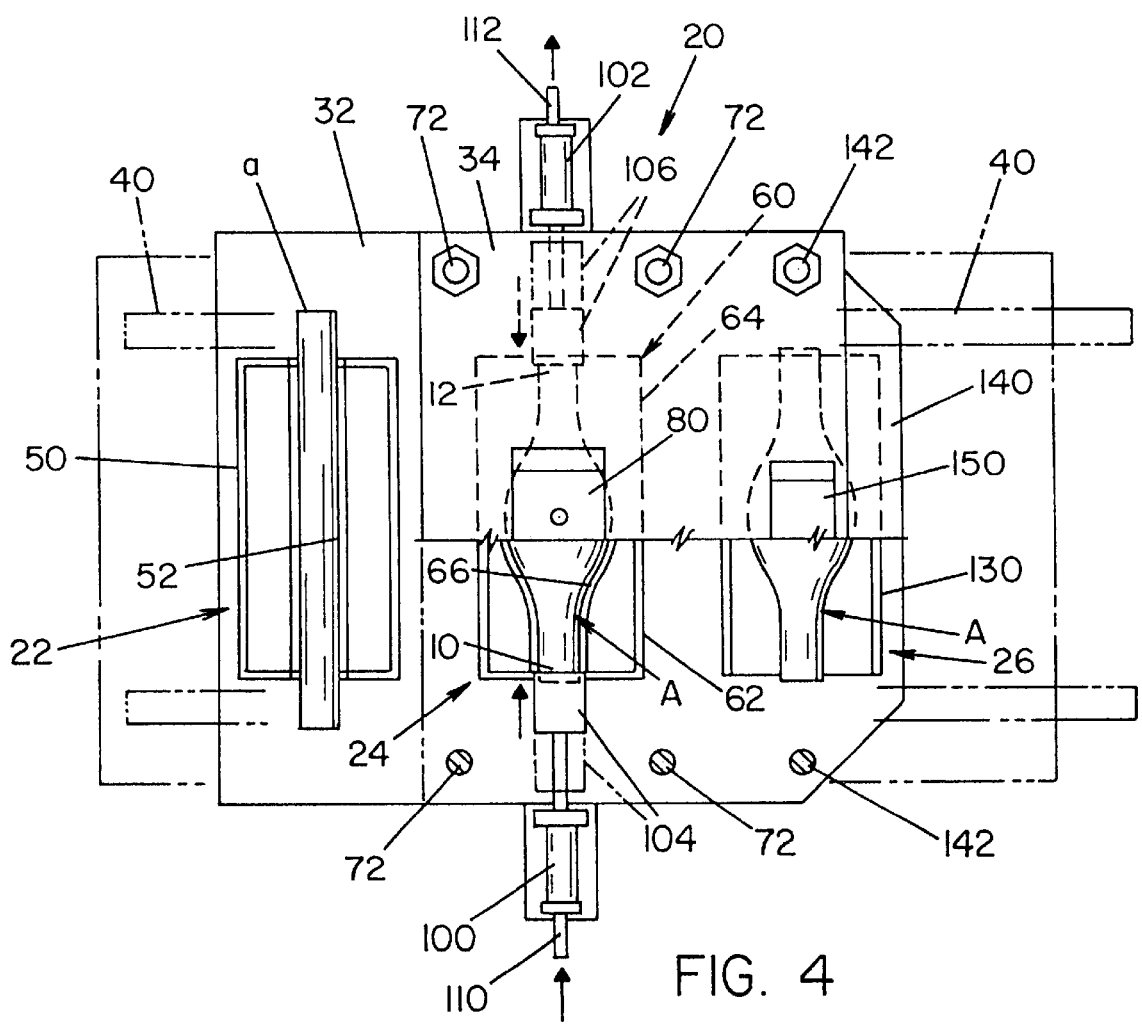
FIG. 4 is a top view of a machine illustrated in FIG. 2.
Figure 2:
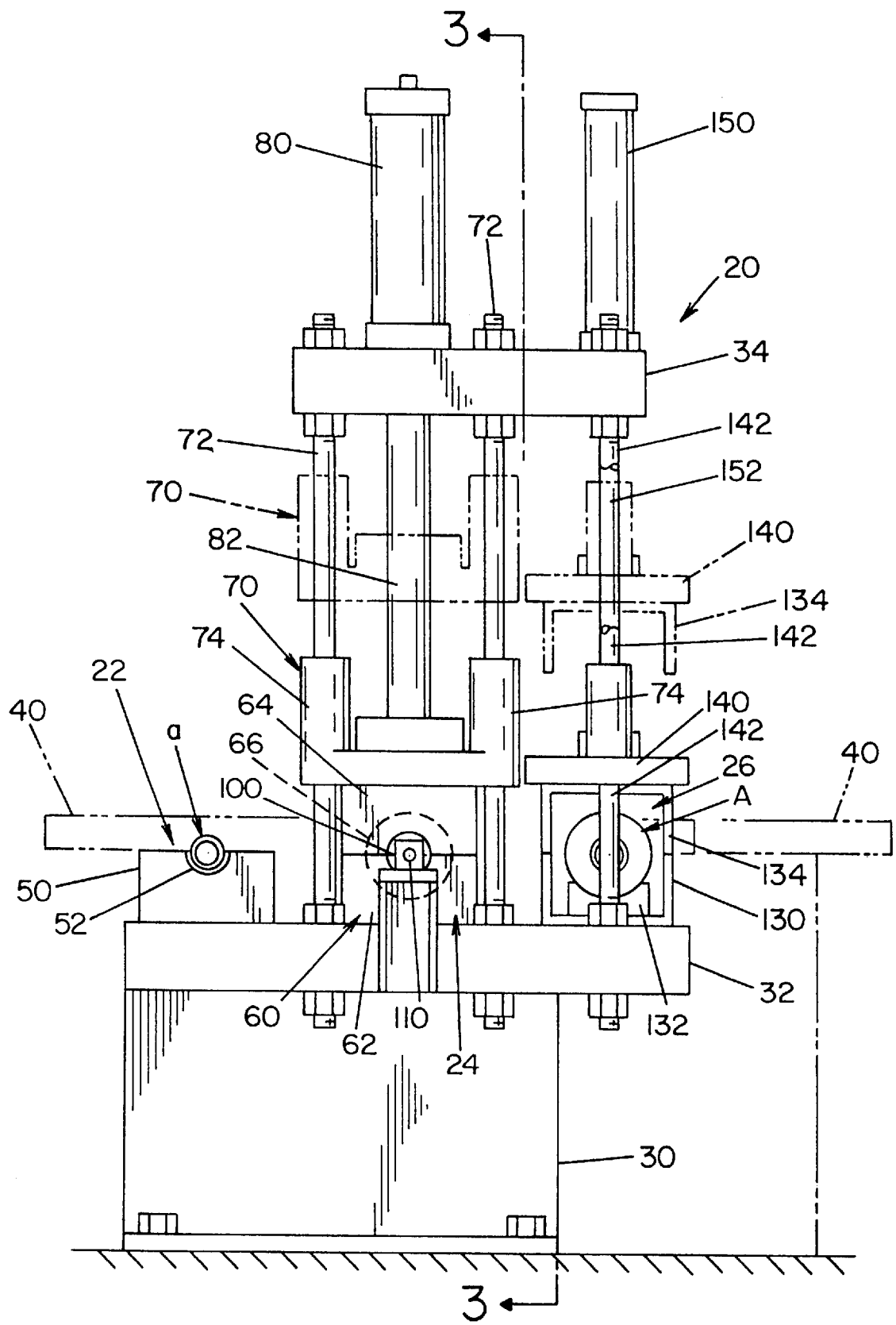
FIG. 2 is a side elevational view showing a machine for practicing the present invention.
Figure 3:
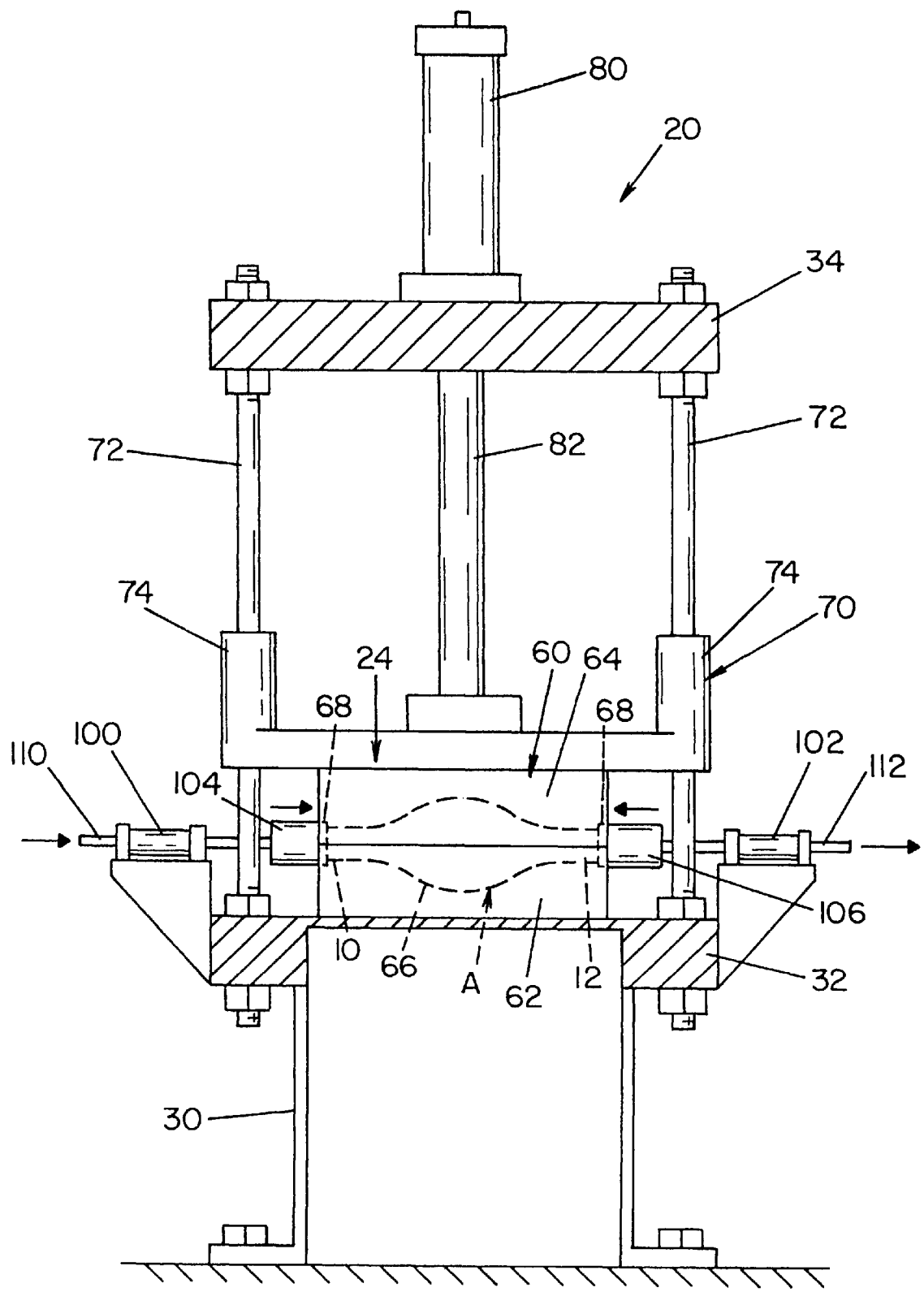
FIG. 3 is a cross sectional view taken generally along line 3—3 of FIG. 2.
Figure 22:
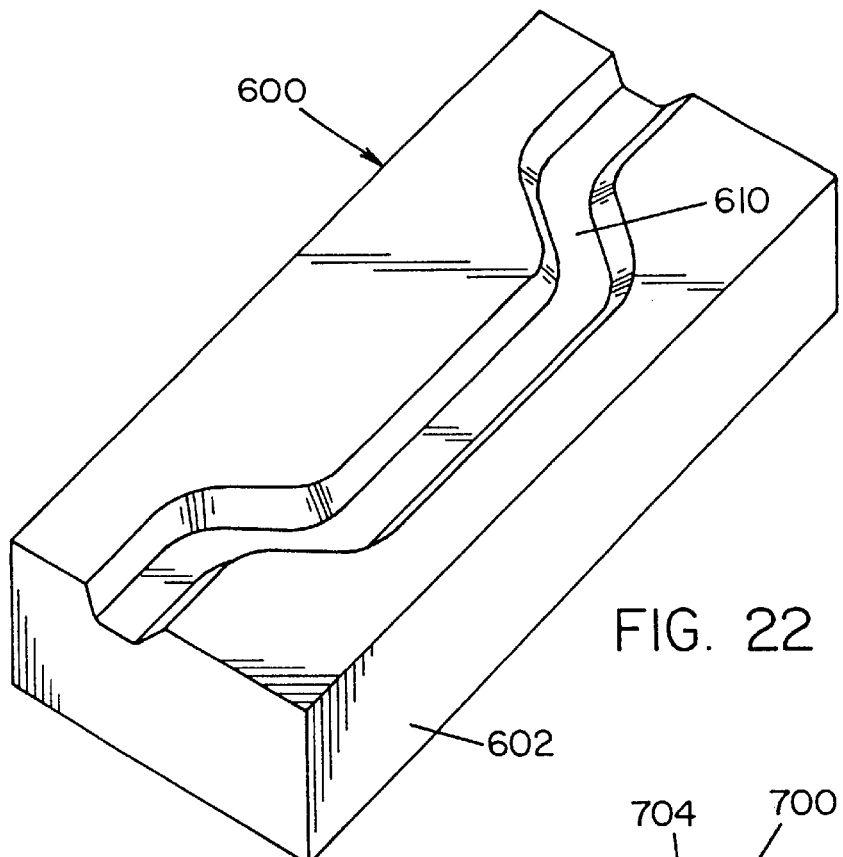
FIG. 22 is a pictorial view showing the preform die used in the preferred embodiment of the present invention with a curved workpiece.

Referring now to the drawings wherein the showings are for the purpose of illustrating the preferred embodiments only and not for the purpose of limiting same, FIG. 1 shows a finished tubular structural component A formed by using the preferred embodiment of the present invention as schematically illustrated as machine 20 in FIGS. 2–4. This part is illustrated as a quite simple shape for ease of discussion. The preferred shape is the workpiece processed by the apparatus shown in FIGS. 22–26. However the disclosure associated with the simple shape of component A applies to all shapes. Machine 20 includes an inlet station 22 for preprocessing a plugged tubular blank which will be described later. This preforming operation may involve bending the tubular blank axially into a preselected general contour or profile as shown in FIG. 22 for the preferred workpiece formed by the invention. The preprocessing of tubular workpiece or blank may involve preforming or heating. Preheating is used in one embodiment of the invention by resistance heating the total blank or workpiece at input station 22. Resistance heating of the blank preparatory to forming by hot gas in accordance with the invention is performed by directing, preferably, an alternating current through the tubular blank or workpiece as it is positioned at input station 22. Resistance preheat can be direct 60 cycle heating. Also, induction resistance heating may be used to change the thermal profile during the preheat step. The frequency can be 60 cycle or higher. It is possible to provide a combination of direct and induction preheat. For illustration purposes, FIG. 2 shows the tubular plugged blank a in station 22, which station can be considered merely a loading station if preforming and/or preheating is not required. In summary, input station 22 is used for preforming, preheating or merely loading. The preforming operation and the preheating operation reduces the amount of time and energy needed to form workpiece or blank a into structural component A at the processing station 24. This station performs the essence of the invention wherein a plugged workpiece or tubular blank a is conductively heated by a plurality of coils or conductors spaced along workpiece a at station 24 while a high pressure inert gas, such as nitrogen or argon, is directed into the tubular workpiece a for expanding the workpiece into a cavity surrounding the workpiece at station 24. After the workpiece a has been inductively heated and formed by inert gas into the desired structural configuration shown in FIG. 1, it is transferred into quench station 26 where a quench liquid, or air is directed toward the outer surface of the heated and formed structural component to cool the component at a rate determining the necessary metallurgical properties of the finished product. In summary, the invention is the expansion of a tubular plugged workpiece a into the desired shape shown in FIG. 1 by inductively heating the workpiece along its length while expanding the workpiece into a predetermined shape determined by a die cavity with inert gas and then immediately moving the hot formed workpiece into a quenching station where a quenching operation creates the desired metallurgical physical properties. By rapid quenching, a hardened structure of the workpiece is created. Slow quenching by liquid or air could be used to temper certain portions along the length of the finished component A. Thus, by inductively heating and selectively quenching the hot metal gas formed structural component, the shape of the component is obtained at the same time metallurgical properties along the length of the structural component are also obtained. This is a novel and heretofore unobtainable result for a metal tubular structural component. The blank when formed of steel has a wall thickness of 0.40–0.35 inches and is preferably less than 0.20 inches. The steel is a single or dual phase, high strength steel. When aluminum is used for the metal formed, 5083 aluminum and several other 5000 series aluminum alloys have been used with a wall thickness of 3 mm.

Although a number of machines and mechanical components could be used for practicing the present invention, the preferred embodiment involves a multi-station machine 20 shown in FIGS. 2–4 having the loading or preprocessing station 22, the actual hot metal gas forming station 24 and the novel quench station 26. In the illustrated machine 20, there is a lower support frame 30 having an upper fixed table 32 overlaid by an upper fixed head 34. Transfer mechanism 40, shown in phantom lines, is a walking beam type of transfer mechanism for shifting the plugged blank a into station 22 for moving the blank or workpiece a to station 24 where it is hot metal gas formed in accordance with the invention and for then moving the formed structural element A to quench station 26 where the heated and formed workpiece is quenched along its length by liquid and/or air quenching. Referring now to initial or loading station 22, a generally rectangular holder 50 has a nest 52 for receiving the plugged tubular blank or workpiece a. The optional preforming shown in FIG. 22 or resistance heating is not illustrated. From loading station 22, workpiece a is moved to the hot metal gas forming station which involves a die set 60 having a lower die member 62 and an upper die member 64 which are brought together to form a cavity or shell 66 defining the desired outer configuration of structural component A after it has been processed in accordance with the present invention. Lower die member 62 is supported on fixed table 32, whereas the upper die member is carried by a platen 70 movable on rods or posts 72 by four spaced bearing housings 74 between a closed lower position shown in the solid lines of FIG. 2 and an upper open position shown by the phantom lines in FIG. 2. Post 72 not only reciprocally mounts the upper die member 64, but also fixes machine head 34 with respect to the lower fixed machine table 32. Movement of die member 64 is accomplished by cylinder 80 fixed on head 34 and joined to platen 70 by rod 82. Movement of the rod 82 by cylinder 80 raises and lowers die member 64 to open and close the die member 60 for loading and unloading station 24. As will be described later, one or both die members include a number of axially spaced induction heating conductors embedded within the die members to heat the metal of blank a to a temperature about 1800° F. The temperature can be varied along the length of the workpiece. Such heating is done by induction heating which raises the temperature of the workpiece by inducing voltage differentials using an alternating current in the coils or conductors surrounding the workpiece during the forming operation. In the preferred embodiment, collects 104, 106 surround the ends 10, 12 which extend outwardly from holes 68 in die set 60 as best shown in FIGS. 3, 4, 17 and 18. These collets are forced inwardly by feed cylinders 100, 102, respectively, so that metal is fed into cavity of shell 66 during the hot metal gas forming process in a manner similar to such in-feed of metal during hydroforming of steel. Inert gas, nitrogen or argon, at high pressure in the range of 200–1000 psi is forced into the heated workpiece to expand the workpiece into shell or cavity 66. The gas is capable of expanding the steel which has a wall thickness in the range of 0.04–0.35 inches and preferably less than 0.25 inches. The metal is heated to a temperature in the general neighborhood of 1800° F. and subjected to an inert gas pressure of 200–1000 psi. This forming process normally takes less than about 20 seconds and preferably about 10 seconds. In practice, the hydraulic pressure from cylinder 80 exerts a compressive force between die members 62, 64 which is about 100 tons. With this high holding force on die set 60, the hot metal gas forming process does not separate die members 62, 64 during the forming operation. When the hot metal has been formed in station 24, cylinder 80 moves upper die member 64 by moving platen 70 upward. After the die has been opened, the formed structural element A is moved by transfer mechanism 40 from station 24 to station 26 best shown in FIGS. 2 and 4.

Lower support base 130 has upstanding quench stands 132 contoured to support and direct quenching fluid against the outer surface of structural component A resting on stands 132. A spray controlling cover 134 is carried on platen 140 movable on post 142 by cylinder 150 on head or crown 34 that actuates reciprocal rod 152. In FIG. 2, cover 134 is shown in its operative position. After the hot metal gas formed structural component A is moved to station 26, cover 134 is lowered to the solid line position and fluid in the form of quenching liquid, or possibly a quenching gas, is used along the length of component A to selectively quench the various portions of the structural component. The desired mechanical and metallurgical properties are created along the length of the final component. This subsequent quenching is useful for controlling the characteristics along the length of the finished product after it has been hot metal gas formed in station 24. Although transfer element 40 can mechanically transfer workpiece a and finished component A between stations 22, 24 and 26, in practice, the transfer has been accomplished manually with the same advantageous results. Machine 20 is only one of many mechanical arrangements that can be used for performing the present invention.

Figures 5, 6:
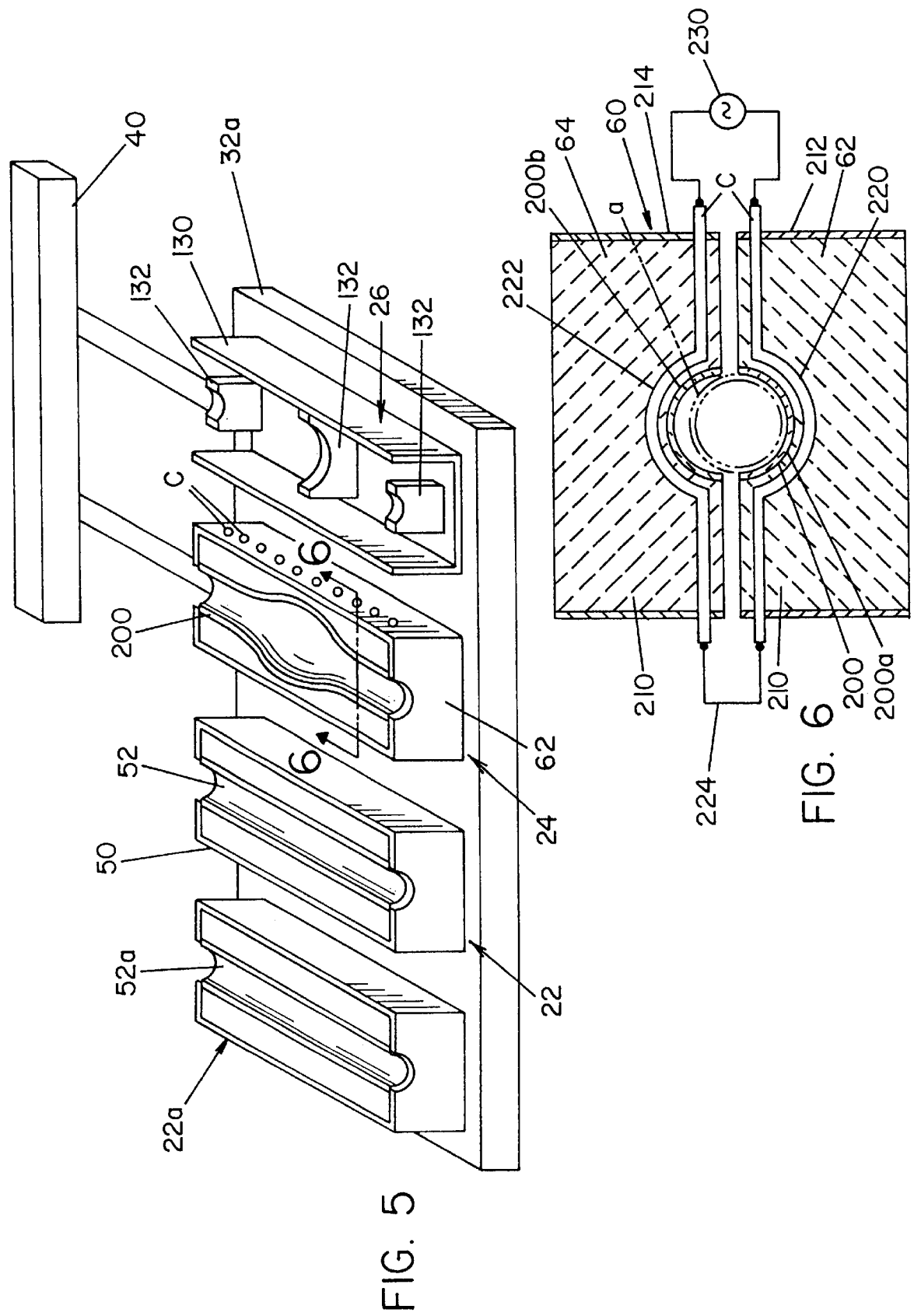
FIG. 5 is a pictorial view of a multi-station platform for processing the workpiece shown in FIG. 1 by using the present invention with an additional processing step.
FIG. 6 is a cross sectional view taken generally along line 6—6 of FIG. 5.
Figure 7:
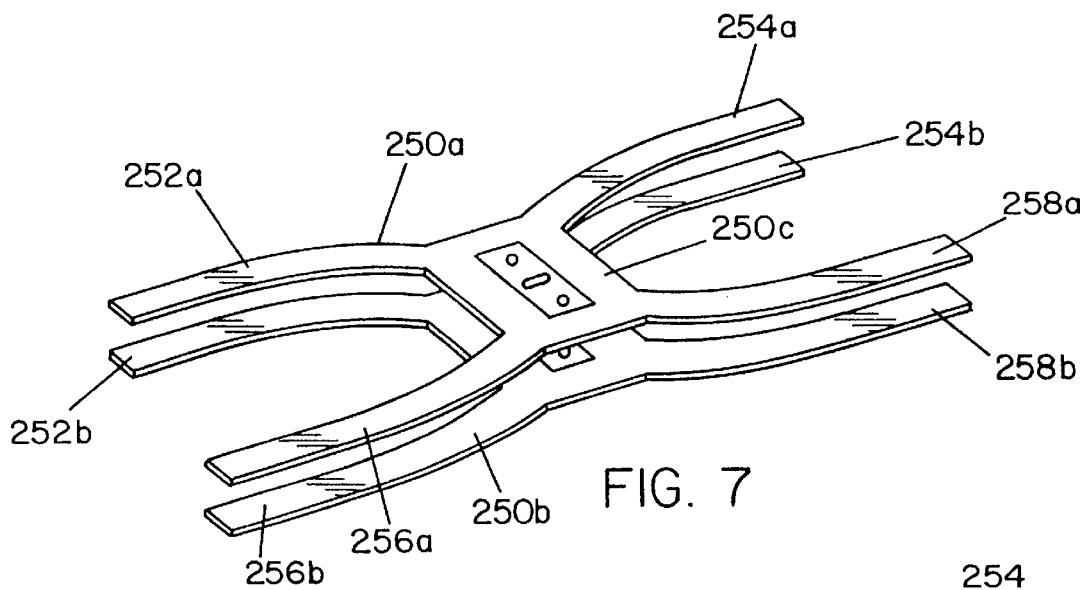
FIG. 7 is a pictorial view of sheet metal portions for making a complex H-shaped tubular blank to be formed by the method of the present invention.
Figure 8:
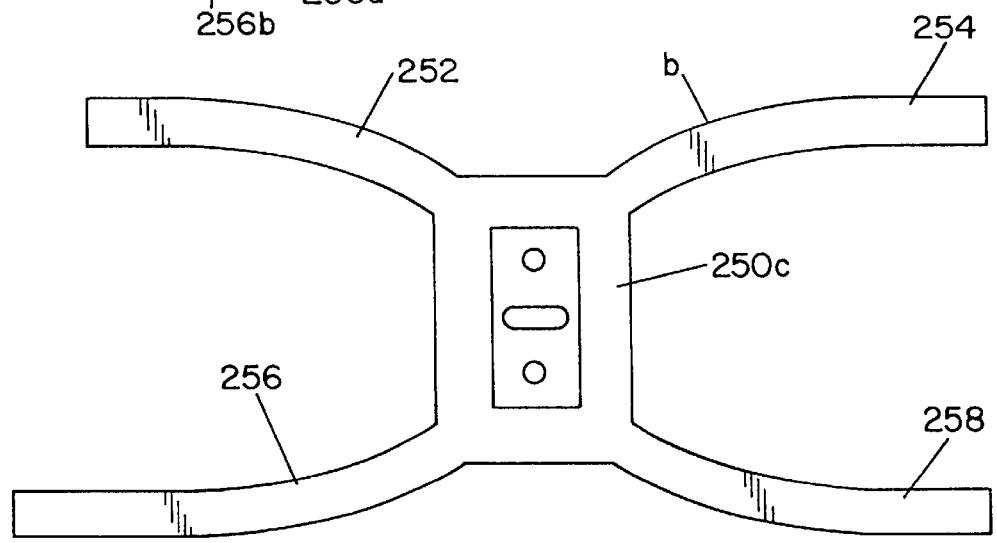
FIG. 8 is a top plan view of the tubular blank using the plates of FIG. 7 after the edges have been welded, but before the blank is trimmed.

A modification of machine 20 is illustrated in FIG. 5 wherein four stations are employed on platform or table 32a. In this modification, a preformed station 22a, such as shown in FIG. 22, is provided with a nest 52a. Nest 52 is used for resistance heating. At station 24, the shape defining shell or cavity 200 of the lower die member 62 is illustrated along with induction heating coils or conductors C. In using this modified machine, workpiece a is placed in nest 52a and shaped into the desired profile. Thereafter, walking beam transfer mechanism 40 shifts the workpiece nest 52 where it is subjected to resistance heating, preferably with A.C. current. The workpiece is then transferred to shell or cavity 200 of die member 62. The upper die member is then closed and the workpiece is hot metal gas formed. The hot formed structural component is then moved to station 26 and quenched as previously described.

Details of die set 60 are shown in FIG. 6 wherein die set 62, 64 include an inner shell or cavity 200 having half shells 200a, 200b, respectively. The shells are formed from a low permeability, rigid ceramic material having a high hardness. In practice, the material is fused silica; however, the material could be selected from the class consisting of silicon nitride, silicon carbide, beryllium oxide, boron oxide and xirconia. In the preferred embodiment, a silicon nitride shell with a wall thickness of $3/8$–$5/8$ is formed with the desired inner surface shape and a coating of dense ceramic layer placed on the surface by sputtering or chemical vapor deposition. Thus, a dense ceramic layer is applied to a non-sintered silicon nitride shell. In an alternative, powdered silica is compressed to about 50%–70% and machined to the desired shape. Then the block is vacuum exhausted while nitrogen is impregnated into the shell. As an aspect of the invention, the low permeability rigid material forming shell or cavity 200 having the desired contour and shape for the finished structural component is selected for its wear resistance and maintenance of the desired shape without deterioration over many forming cycles. In the past, a hard, rigid shell was not used for creating the forming cavity between die member 62, 64. By using a separate rigid shell for the cavity in the die set, a less expensive and compressive force resisting fill material 210 can be selected for the body portion of die members 62, 64. Fill material 210 is non-magnetic and compression resistant. Fused silica or even cement has been used successfully since shell 200 is the precision component. Fill material 210 is selected for its pressure resistance and its ability to maintain shell 200 rigidified. Ceramic fill material 210 is selected for its compression resistance characteristics and is a castable ceramic having strength and hardness substantially less than the rigid ceramic shell 200. In practice, any of a number of castable ceramics, such as fused silica, or cement is employed for the support of rigid, hard shell 200. Die members 62, 64 are held together with a framework 212, 214 which is a non-magnetic material, such as aluminum or stainless steel. The 100 tons of pressure is applied between castable ceramic material 210 of die members 62, 64 for holding rigid, hard shell or cavity 200 in place during the forming process in station 24.

Ceramic fill material 210 encapsulates and supports the number of axially spaced conductors C forming the induction heating mechanism of die set 60. In the preferred embodiment, as shown in FIG. 6, conductors C include arcuate portions 220, 222 conforming to the outer configuration of shell 200. Conductors or coils C are connected in series, as shown by connector 224 and are powered by an alternating current power source 230 which, in practice, operates at a frequency greater than about 3 kHz and preferably greater than about 10 kHz. Axially spaced conductors C are joined by connectors 224 to place them in series with the power supply 230 in accordance with standard induction heating practice. Encircling coils in shell 200 are formed by joining upper and lower conductors C, as shown in FIG. 6. Various arrangements can be used for connecting the set of conductors C in die member 62 and die member 64. The conductors extend across the dies and are connected in a series circuit with a power supply, such as power supply 230. This power supply is an inverter in practice. Die set 60 is opened and workpiece a is placed in the cavity defined by shell 200. Then the die set is closed to combine workpiece a in cavity or shell 200 where it is heated inductively along its length and formed by introducing hot inert gas. In practice the conductors for the induction heating of the workpiece are non-magnetic, high resistivity steel (Inconel) tubes with water cooling. These conductors have greater strength and are better suited modules than copper tubes.

Figure 9:
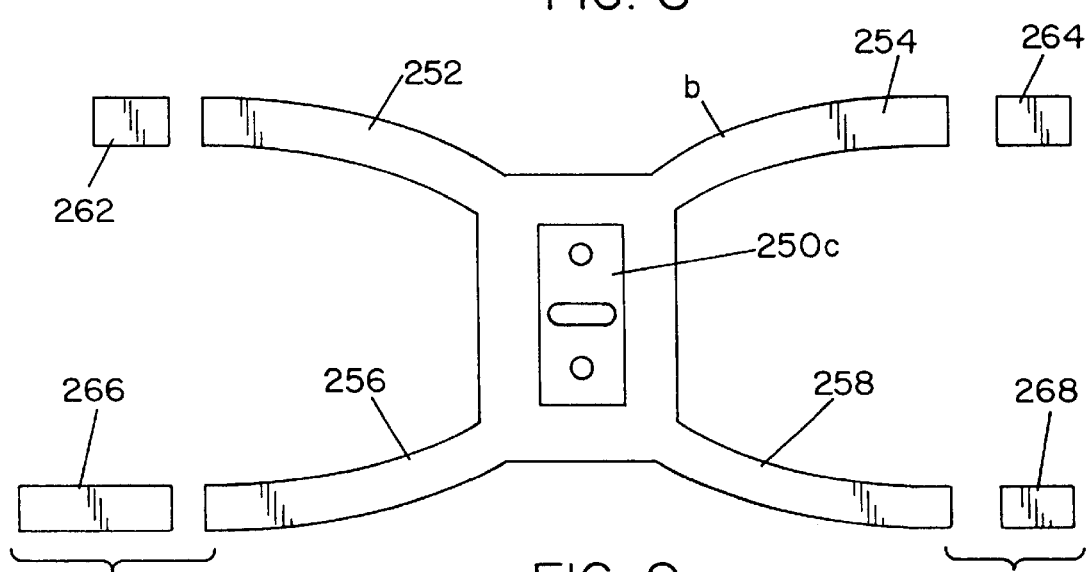
FIG. 9 is a view similar to FIG. 8 with the tubular blank with the four legs trimmed to the desired length.

The present invention can be used for producing a large variety of structural components. To illustrate the versatility of the present invention, an H-shaped structural element B is formed by the method of the present invention. Tubular blank b is shown in FIGS. 7–12. Two H-shaped steel plates 250a, 250b with a laser welded center portion 250c are joined together in a manner where legs 252a, 254a, 256a, 258a are seam welded to legs 252b, 254b, 256b and 258b, respectively to form tubular blanks identified as legs 252, 254, 256 and 258 in FIG. 8. The outer edges of the plates are laser welded together as shown at seam W in FIG. 10. Overlying welded legs 252 and 254 form a single hollow workpiece. In a like manner, seam legs 256, 258 form a single hollow workpiece. These tubular legs are like workpiece a shown in FIGS. 2 and 4. Center portion 250c is welded together to form a generally flat structural element, but it does not constitute necessarily a portion of the tubular workpiece to be formed. After seam welding legs 252, 254, 256 and 258 to form workpiece b, the legs are trimmed to the desired length by removing excess portions 262, 264, 266 and 268 by trimming the ends of the respective legs. This trimming action produces a workpiece b, as shown in FIG. 9, which workpiece is in the form of two generally parallel tubular blanks. In accordance with the invention, plug 270, having a wedge shaped nose 272, is forced hydraulically into the end of each of the legs 252, 254, 256 and 258. Each of the plugs 270 includes a gas inlet 274 with a flared gas passage 276. As shown in FIGS. 10–12, plugs 270 are forced in the end of each of the legs so gas G can be forced into each of the legs to expand the legs into the shape of the H-shaped shell of die members 60, 62 having shells or cavities formed in accordance with the desired shape of structural component B illustrated in FIG. 13. During the forming process, the workpiece is heated inductively by coil 280 encircling legs 252, 256 and driven by high frequency power supply 282. In a like manner, induction heating coil 290 encircles legs 254, 258 and is energized by a high frequency power supply 292. In accordance with an aspect of the invention, the coils 280, 290 are operated at different cycles 50 of the respective legs being formed are heated differently, in accordance with an aspect of the process of the invention. Thus, portions 300, 302 of legs 252, 256, respectively, are heated substantially less than portions 304 and 306 of legs 254, 258. This representation of the present invention illustrates that the induction heating equipment associated with the die set allows processing of the workpiece being formed at different temperatures to obtain the desired forming rate. It is part of the invention that a greater portion of legs 254, 258 be heated during the forming process than the portion being heated in legs 252, 256. However, all of the metal being formed must be at a temperature of at least about 1400–1500° F. This is a novel concept of heating portions of the workpiece differently. In the past, when induction heating was used for superplastic deformation of sheet material, the total sheet material was heated the same. Thus, the requirement for different heating at different sections could not be accommodated by use of the prior superplastic heating processes used for flat plate material.

Figure 14A:
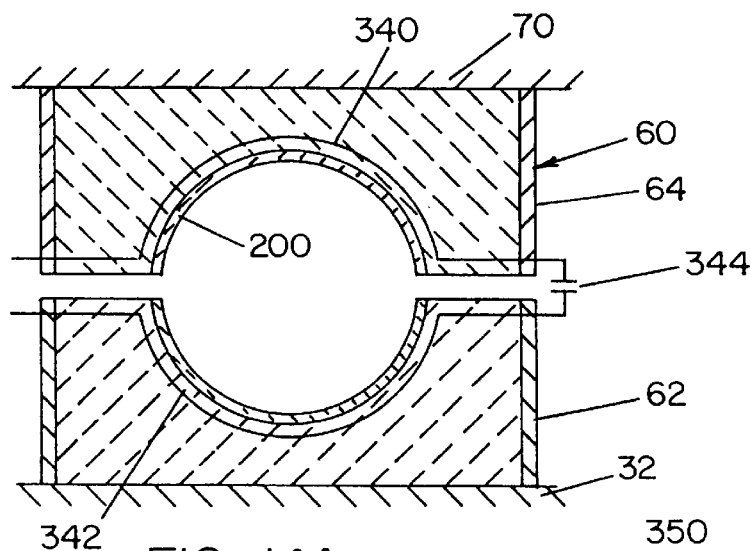
FIG. 14A is a cross sectional view of the two die members used in practicing the present invention illustrating the use of a connector for joining the conductors, shown as solid lines, in the induction heating mechanism of the invention.

A primary aspect of the invention is the ability of the induction heating equipment associated with the die set 60 to selectively heat differently different portions of the tubular blank or workpiece being formed by high pressure gas. As mentioned above, this ability to "tune" the induction heating along various sections of the workpiece being formed is novel and has not been done previously. Variations in the induction heating of the workpiece being formed by high pressure gas in accordance with the invention can be accomplished by using various induction heating arrangements. One of these arrangements is illustrated in FIG. 14. The cross sectional shape of the forming shell includes a dome portion 310 in upper die member 64 and a generally flat portion 312 in lower die member 62. It is desired to heat the portion of the workpiece being formed greater adjacent the dome shaped portion 310. Consequently, axially spaced conductors 320 with water passage 322 are spaced along the dome portion of the shell in upper die member 64. These conductors 320, several of which are aligned along the axis of the workpiece, each have an arcuate segment 330 with straight legs 332, 334. There are no conductors adjacent flat portion 312 in lower die member 62. By using this configuration, induction heating is accomplished at the top side of the workpiece that is going to have the most movement of metal during the forming process. A generally circular workpiece a is placed between shell potions 310, 312 and is expanded by gas as it is being heated by induction heating on the side adjacent the dome portion through the induction heating effect of the arcuate segments 330 of axially spaced conductors 320. This implementation of the present invention shows how the heating can be accomplished along the length of the workpiece at different heating cycles or different magnitudes. This can be done by encircling conductors such as conductors 340, 342 placed in series by connector 344 as shown in FIG. 14A, by the arrangement shown in FIG. 14 or by the selective heating arrangement illustrated in FIG. 14B.

Figure 14B:
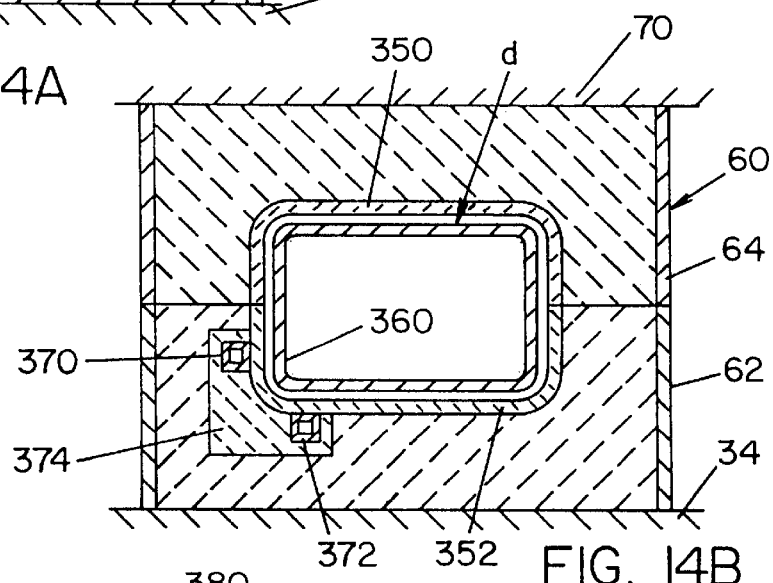
FIG. 14B is a cross sectional view illustrating induction heating of a selected area of the tubular blank as it is being formed in the die members.
Figure 14C:
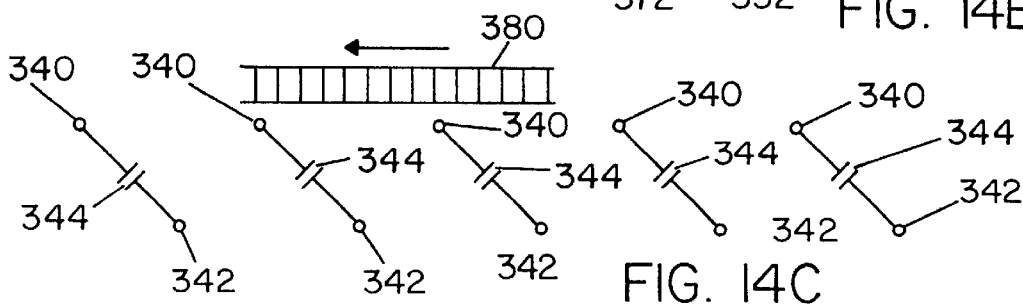
FIG. 14C is a schematic view of a flux yoke to selectively increase the induction heating in specific areas along the tubular blank as the blank is being formed.
Figure 14D:
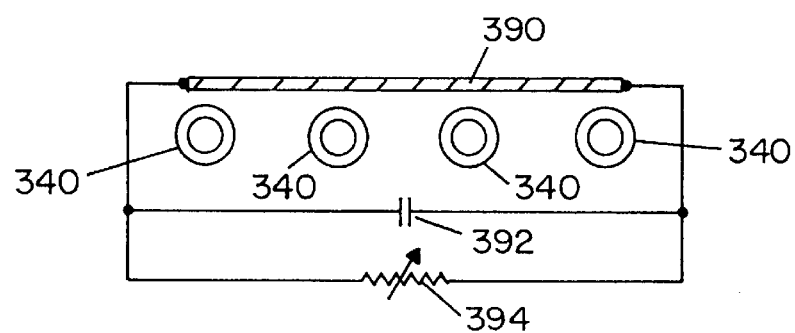
FIG. 14D is a schematic view illustrating the use of a Faraday shield shiftable along certain areas of the induction heating conductors to alter the heat profile along the length of a blank being formed.

In FIG. 14B, a generally rectangular tubular workpiece d is to be formed in half shells 350, 352 which forms an encircling configuration when die set 60 is closed. In this implementation of the present invention, corner 360 of workpiece d is to be heated during the forming process. This is accomplished by conductors 370, 372 at the opposite ends of flux concentrator 374 formed of a high permeability material, such as Ferrocon. As shown in FIGS. 14, 14A and 14B, induction heating of selected portions along the length of the workpiece being formed by high pressure gas is used to control the forming process. This is also employed for the purposes of controlling the metallurgical properties of the final product, as will be explained later. By changing the conductors 340, 342 along the length of the workpiece being formed, as shown in FIG. 14A, a different amount of heating can be accomplished along the length of the workpiece or on one side of the workpiece. Another arrangement for changing the heating effect along the length of the workpiece is illustrated in FIG. 14C wherein the axially spaced conductors 340 are joined in series with conductors 342 by connectors 344 as previously described. In one or both of the die members, there is provided a flux yoke 380 formed of high permeability material which is located along the axial length of the workpiece to shunt the induction heating effect of the coils 340, 342. In this manner, throughout the length of the workpiece, a constant encircling coil for induction heating is provided. This is the preferred arrangement. To change the amount of heating caused by this continuous encircling coil, the die set is provided with a flux yoke 380 positioned axially along the workpiece. This changes the heating effect at various axial positions along the workpiece without really changing the induction heating coil arrangement. Another system for changing the induction heating is illustrated in FIG. 14D where Faraday shield 390, including a capacitor 392 and an adjusting resistor 394, is provided at various locations along the length of the workpiece. The effect of the Faraday shield is adjusted at various positions to decrease the amount of induction heating caused by certain portions of the coil encircling the workpiece, as schematically illustrated in FIGS. 14A, 14C. As illustrated in these figures, a variety of electrical options are available to change the amount of heating along the length of the workpiece or at different sections of the workpiece while the workpiece is being expanded by gas in accordance with the invention. The coils or conductors C are spaced above shell 200 and the heating effect is changed to control the amount of, and location of, different heating effects.

The versatility of tuning the induction heating along the length of the workpiece is illustrated in another embodiment of the invention wherein a tubular workpiece is to be formed into a complex tubular structural shape as defined by shell 200' in die members 62', 64' of die set 60' as shown in FIG. 15. This shell will cause the tubular workpiece to have different diameters and shapes in areas 402, 404, 406, 408 and 410. In these different areas, a different amount of heat is required for deformation and the desired characteristics of the workpiece. Consequently, the die members are provided with a plurality of encircling induction heating coils 402a, 404a, 406a, 408a and 410a, respectively. These encircling coils are spaced axially along the shell or cavity 400 defining the final outer shape of the tubular structural component being formed by using the present invention. In accordance with this aspect of the invention, each of the separate coils has a specific frequency and a specific power level. Several power supplies PS1, PS2, PS3, and PS4 are provided to create the different frequencies and power levels for coils 402a–410a. As illustrated, power supply PS1 has a frequency F1 and a power level P1. This power supply is connected to encircling inductors 402a and 408a. In the same fashion, power supply PS2 has a frequency F1 which is the same as PS1 but a different power level P2. This power supply energizes encircling coil 410a. In a like manner, power supply PS3 has a frequency of F2 and a power level of P3. This power supply drives encircling inductor 404a. In a like manner, power supply PS4 has a frequency of F3 and a power level P4 for energizing encircling coil 406a. By changing the heating frequency and power level the heating cycle during the forming process is modulated and changed along the length of the workpiece. This is used not only for controlling the amount of heat for the purposes of optimizing the forming operation, but also to optimize the metallurgical processing of different sections of the workpiece. It is necessary to raise the temperature of the total length of the workpiece being formed to a temperature in the range of 1400° F.–1800° F. Consequently, the areas of shell 200' without coils or conductors will be short if they exist at all. It is preferred to use a large number of conductors with the heating effect changed, such as shown in FIG. 15 but by various arrangements.

Figure 16:
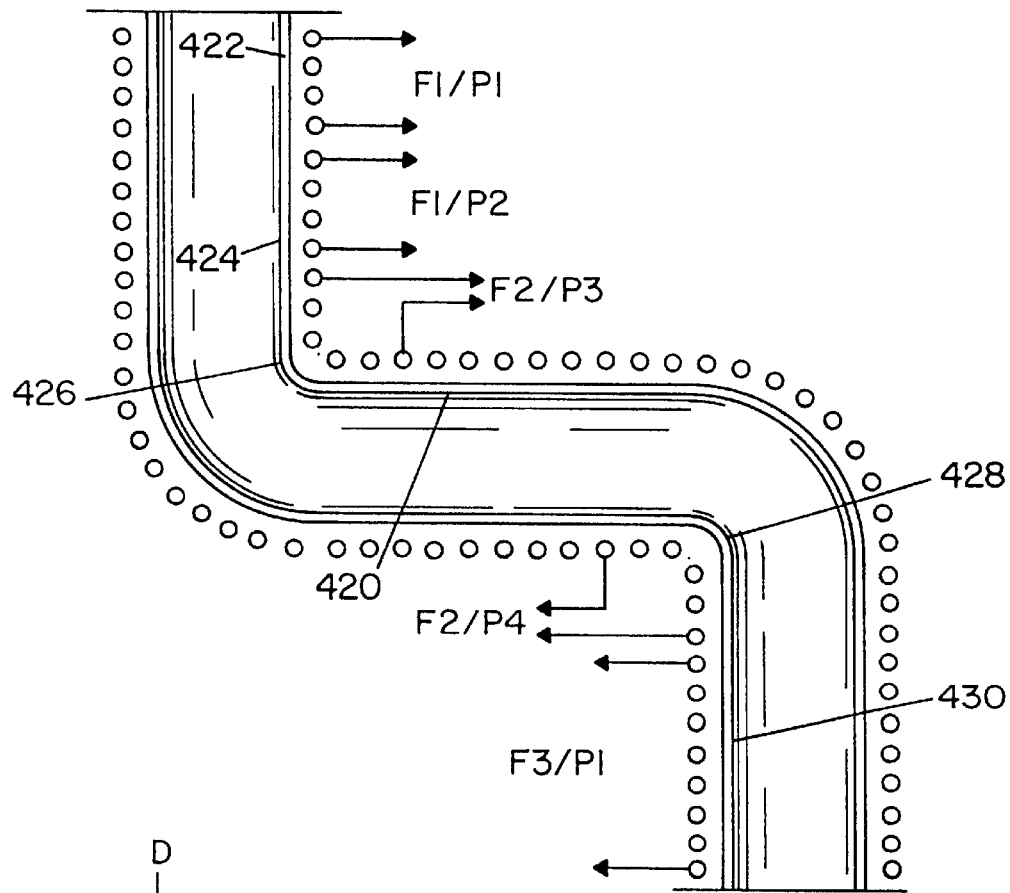
FIG. 16 is a schematic cross sectional view of a die member for forming a tubular blank having a undulating profile wherein selective induction heating coils or conductors are positioned at different areas in the die member to inductively heat the tubular workpiece during the forming operation using different induction heating cycles.
Figure 17:
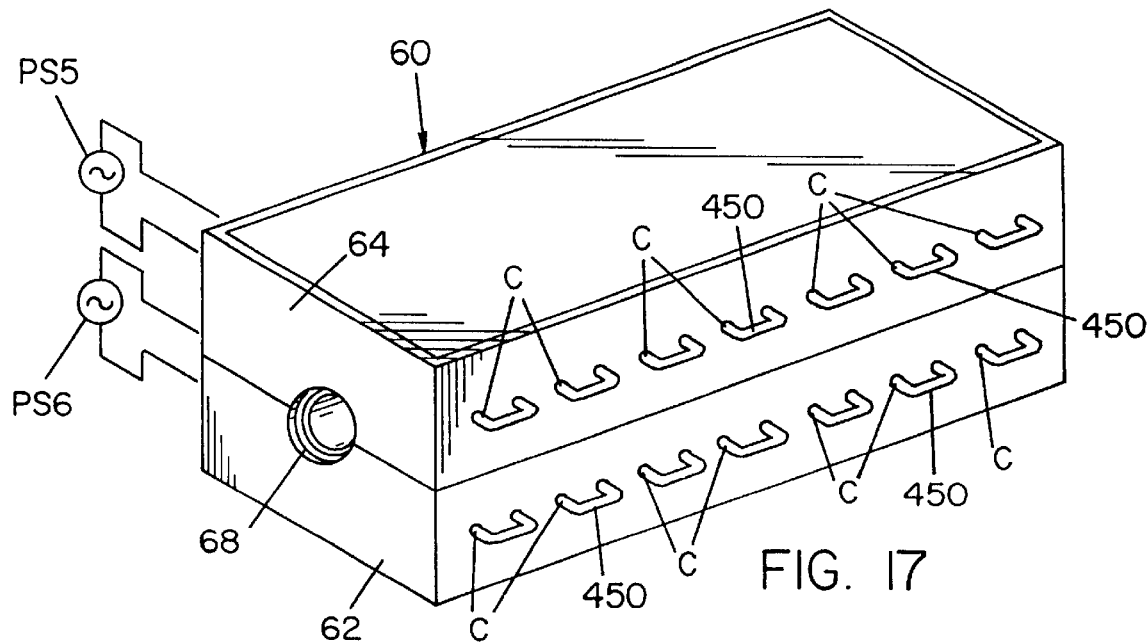
FIG. 17 is a pictorial view of a closed die set for use in practicing the present invention, wherein the coils or conductors along the length of the die set are connected in series in each of the die members.
Figure 18:
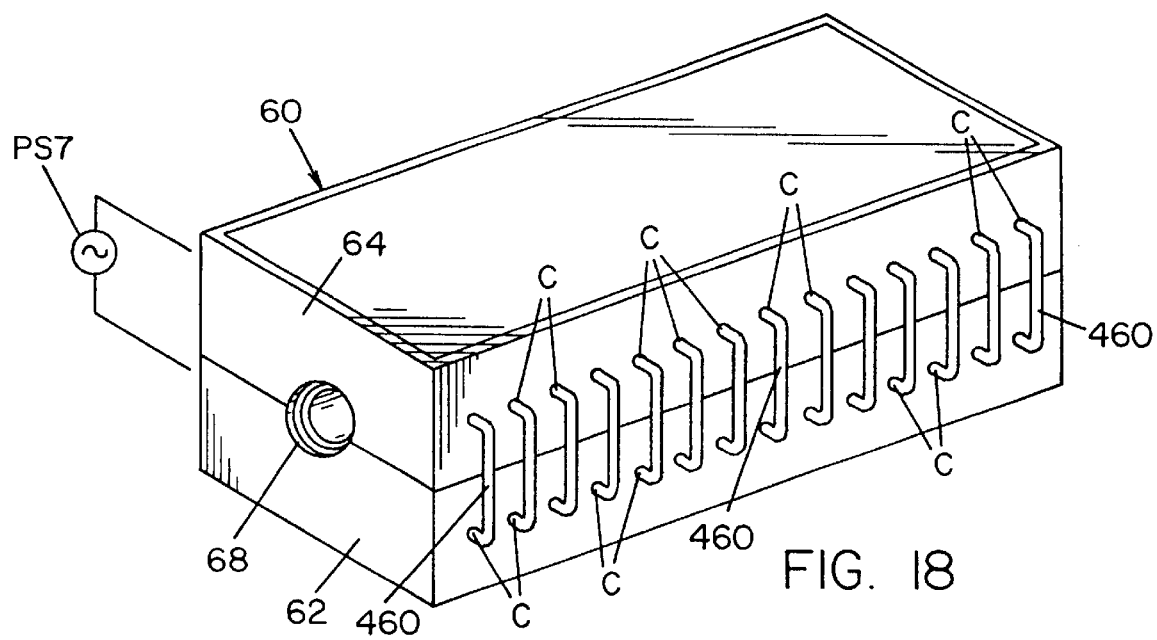
FIG. 18 is a pictorial view, similar to FIG. 17, wherein the conductor or coils are connected in series from one die member to the other. This requires flexible connectors or other movable connectors to allow separation of the die members for loading and unloading the tubular blank.

Another feature employed in an alternative of the present invention is illustrated in FIG. 16 wherein shell 420 has a modified profile, but a uniform cross section. In this embodiment of the invention, an induction heating coil is provided around the total length of the workpiece being formed. This is the preferred arrangement as opposed to the embodiment of the invention shown in FIG. 15 wherein selective areas of the workpiece are provided with encircling inductors. Where all areas have encircling inductors, the heating along the length of the workpiece is accomplished by using different power supplies as shown in FIG. 15A. Different regions of the workpiece can be heated sequentially, or with adjustable heating power, to achieve desired strain distribution. However, as shown in FIG. 15, it is also possible to not energize a portion of the encircling inductors or energize a portion for a shorter time at a lower power. The shell 420 is divided into sections 422, 424, 426, 428 and 430. Between sections 426 and 428 there are encircling inductors that could be used for induction heating; however, in accordance with an aspect of the invention, these induction heating coils are not subject to being energized. Thus they do not cause induction heating, even though they are present. Such uniform distribution of the induction heating coils as used in the preferred embodiment is illustrated in FIGS. 17 and 18. Conductors C are connected in series by connectors 450 and powered by separate power supplies PS5 for upper die member 64 and PS6 for lower die member 62. In FIG. 18, flexible connectors 460 are between the upper and lower die member in a single power supply PS7 is used. In FIG. 18, connectors 460 are flexible to allow for opening and closing of the die set for loading and unloading the workpiece. Opening 68 at the end of the die set accommodates protruding ends 10, 12 of the workpiece as schematically illustrated in FIG. 1. These ends are necessary for plugs to introduce the high pressure inert gas.

Figure 19:
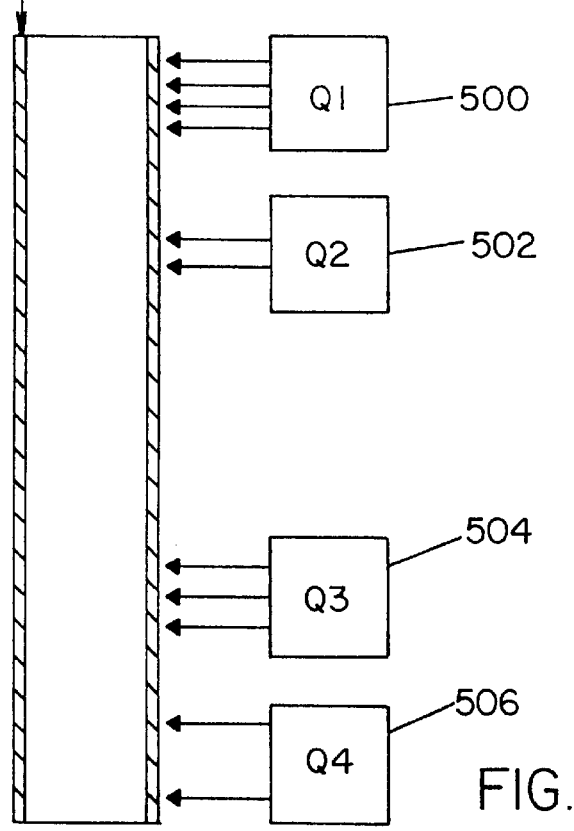
FIG. 19 is a schematic view of the tubular structural component after it has been formed and inductively heated along its length with selected quenching stages illustrated.

Another aspect of the present invention is controlled cooling after hot forming at station 26. The controlled cooling process is either a quenching operation, or an operation cooling the workpiece at a reduced rate, depending on the metallurgical characteristics of the workpiece material and the performance requirements of the final structure. The use of the terminology of "quench" is to represent the general on-line heat treating process and to explain the capability of the new forming process for optimizing the material performance. This feature is schematically illustrated in FIG. 19 wherein a finish hot formed tubular workpiece is positioned in the quench station 26. Along the length of the workpiece different quenching orifices are used. This is illustrated as quench station 500, 502, 504 and 506, each of which is individually controlled in either liquid or gas quenching. By using a precise quenching cycle with a specific heating cycle during the processing of the workpiece D, the metallurgical properties of the finished product are controlled. The modulation of induction heating along the length of the workpiece, in combination with the precise control of the quenching along the workpiece, creates an improved finished product wherein the metallurgical properties along the workpiece are optimized based upon the desired amount of heating, the temperature of the heating cycle and the quenching cycle. This is a further aspect of the present invention and is completely different than procedures heretofore used in gas forming of metal sheets. It is preferred to use steel in the invention, since steel has the capability of modified metallurgical properties along its length.

The cooling or quench station 26 sometimes uses distortion controlling restraints to give size control. When cooling aluminum a high rate of uniform cooling, as by sprays, is used with the mechanical restraints.

Figure 20:
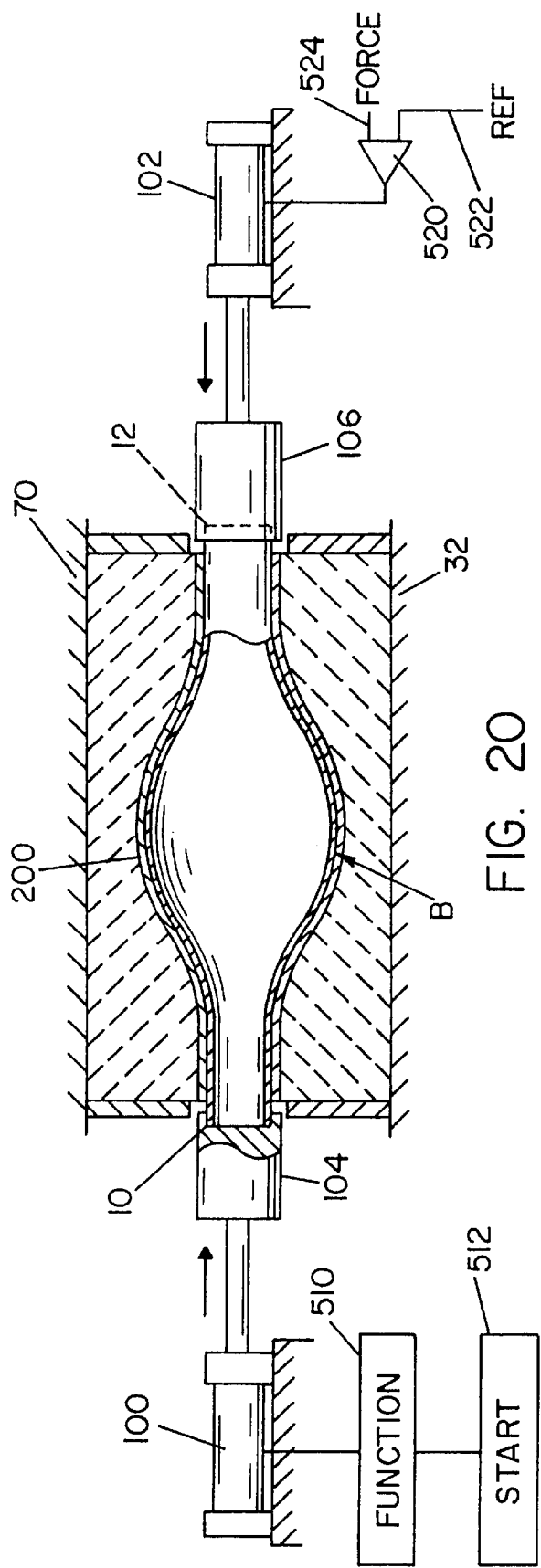
FIG. 20 is a side elevational view illustrating an aspect of the machine for in-feeding a metal as the tubular blank is being formed into the tubular structural component.
Figure 21:
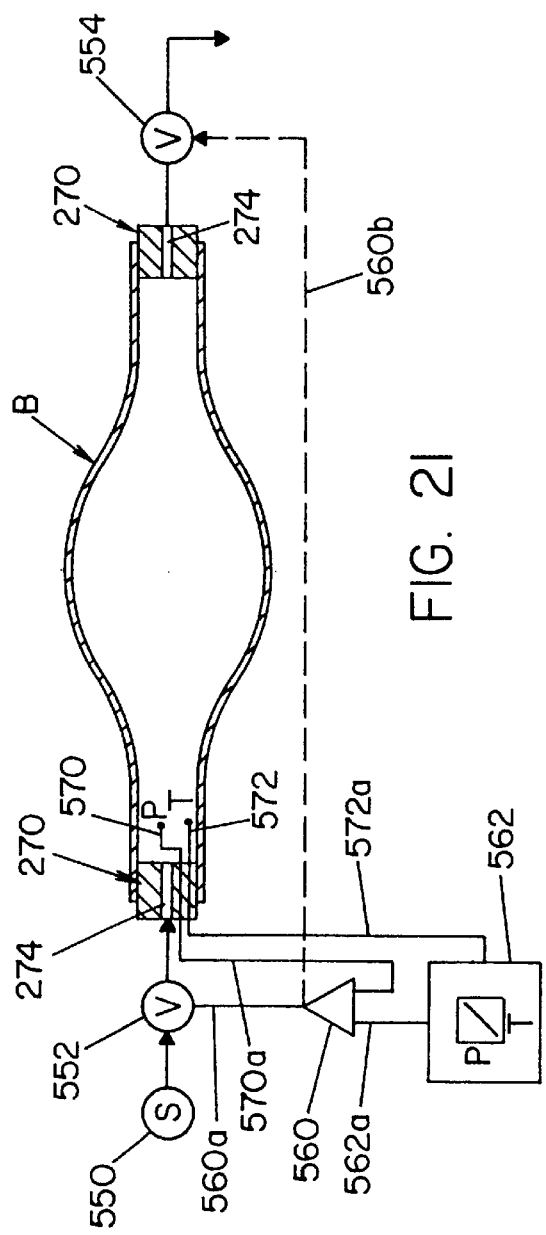
FIG. 21 is a view similar to FIG. 20 showing control elements in block diagram form as used in a control system of the preferred embodiment of the present invention.

The invention uses the concept of positively feeding metal into the cavity of the die set as the metal is formed. This concept is schematically illustrated in FIG. 20 wherein a function generator 510 controls servo cylinder 100 forcing the collect 104 inward slightly during the hot metal gas forming process. The process is started as indicated by block 512. In a like manner, cylinder 102 is moved inwardly by a signal from error amplifier 520 having a sensed force signal in line 524. The level of the actual force applied by cylinder 102 is compared to the level of a reference signal in line 522. The error signal controls servo cylinder 102. The illustration in FIG. 20 is representative. This concept is also used in hydroforming and will be used in practicing the present invention when further implementation of the invention is made. In accordance with an aspect of the invention schematically represented in FIG. 21, plugs 270 have gas inlets or outlets 274. Gas supply 550 provides an inert gas such as argon at a pressure between 200–1000 psi. This gas is directed to workpiece B by an inlet valve 552. An exhaust valve 554 allows decrease in the internal pressure of workpiece B. Valve 552 increases the gas pressure while exhaust valve 554 decreases the pressure. These valves are controlled by an error amplifier 560 having an outlet 560a that operates valve 552. In the alternative, line 560b controls exhaust valve 554. Function generator 562 provides one input 562a to error amplifier 560. The other input 570a is created by pressure sensor 570 within workpiece B. Pressure sensor 570 provides a signal in lines 570a that is compared with the output of function generator 562 at line 562a. This determines whether, at a given temperature, represented by the signal in line 572a from sensor 572 additional pressure or less pressure should be provided in workpiece B. Consequently, the pressure is maintained at the desired selected level associated with a given temperature. Control arrangements, both analog and digital, can be used in the preferred embodiment of the present invention.

Figure 23:
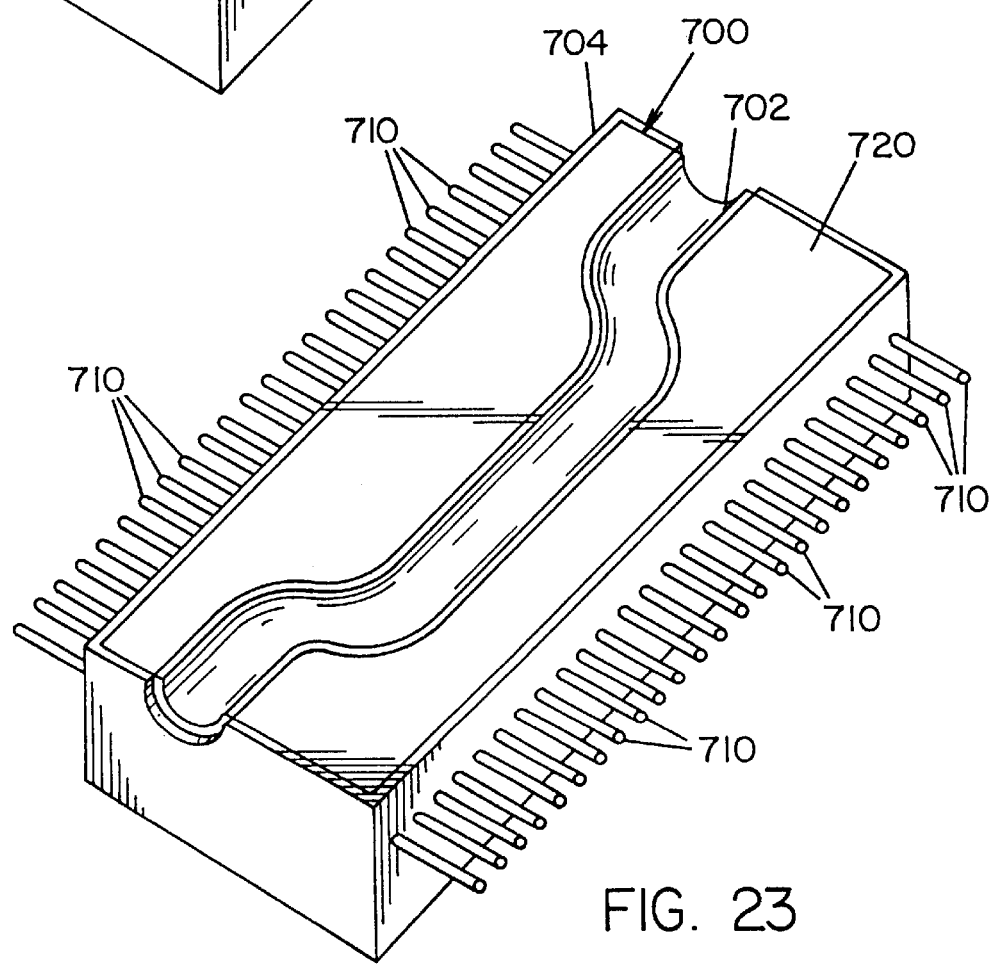
FIG. 23 is a pictorial view of the lower die member used to form a curved workpiece preformed by the preform die in FIG. 22.
Figure 24:
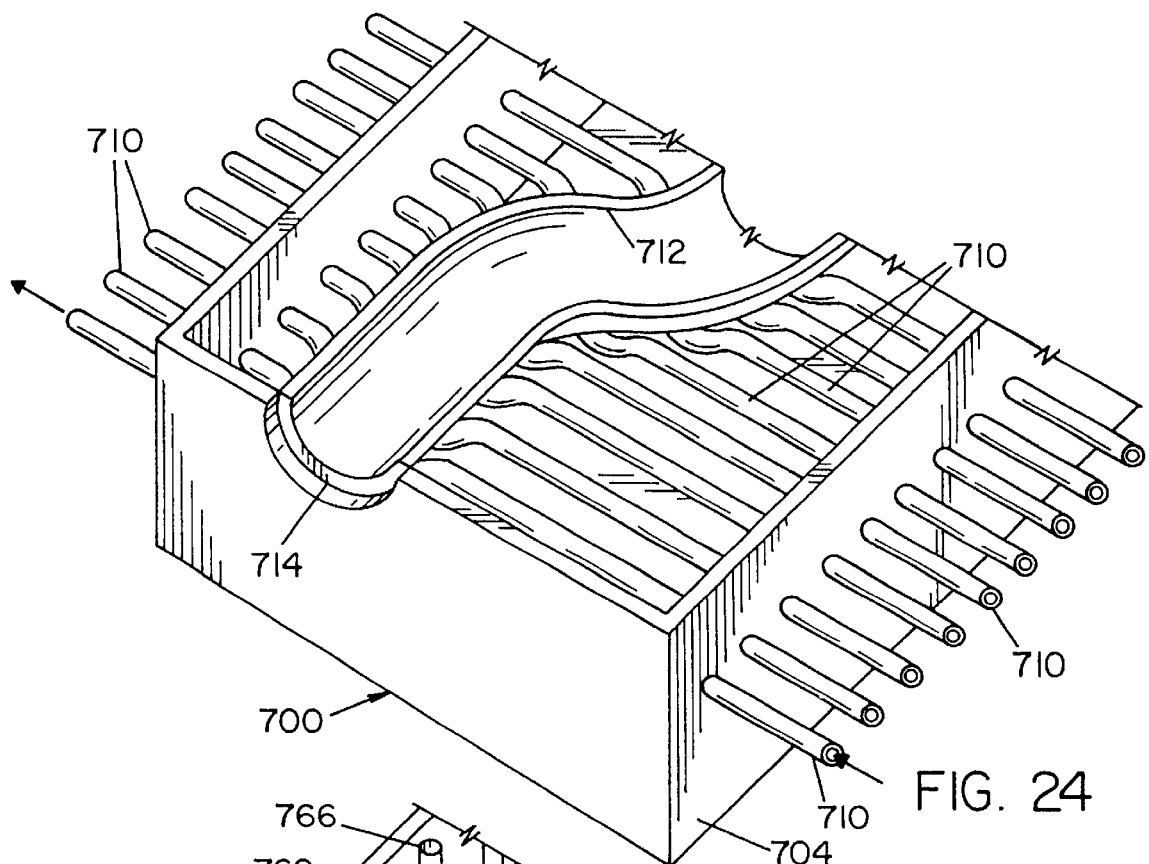
FIG. 24 is a partial pictorial view illustrating the end portion of the lower die member used in the preferred embodiment of the present invention.
Figure 25:
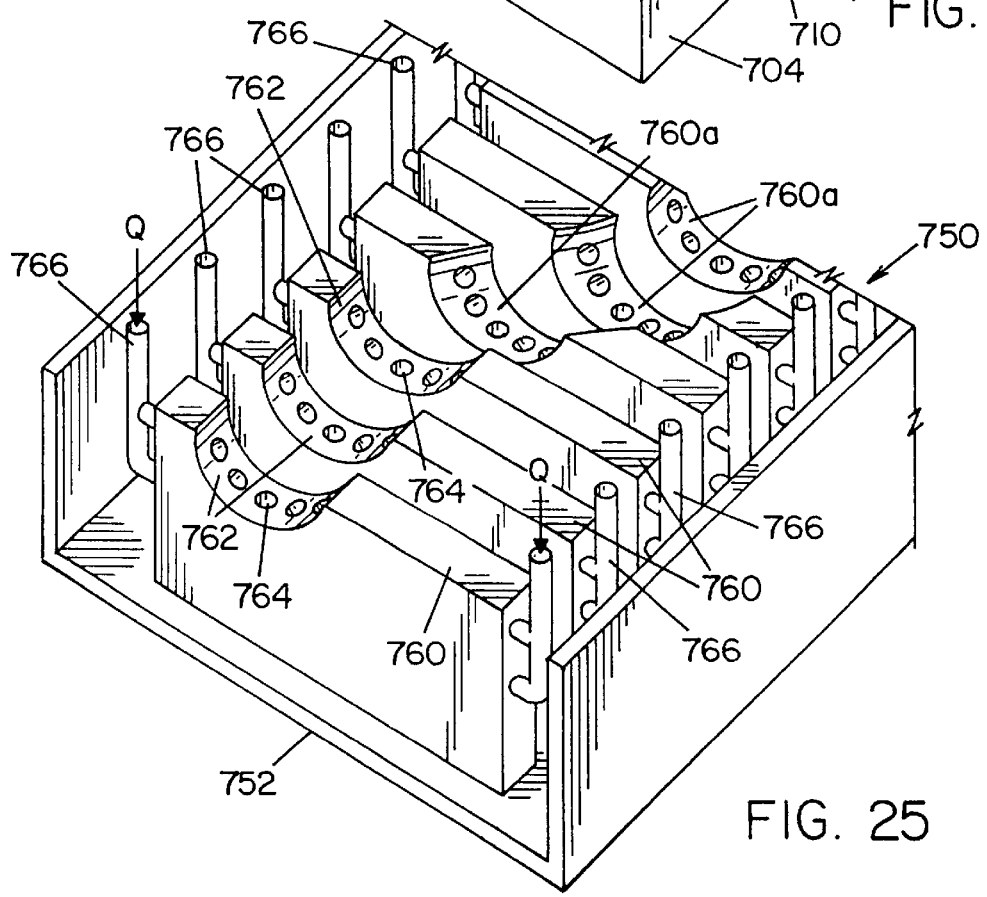
FIG. 25 is a pictorial view of the end portion of the quench station for selectively quenching previously inductively heated portions of the final tubular structural component.
Figure 26:
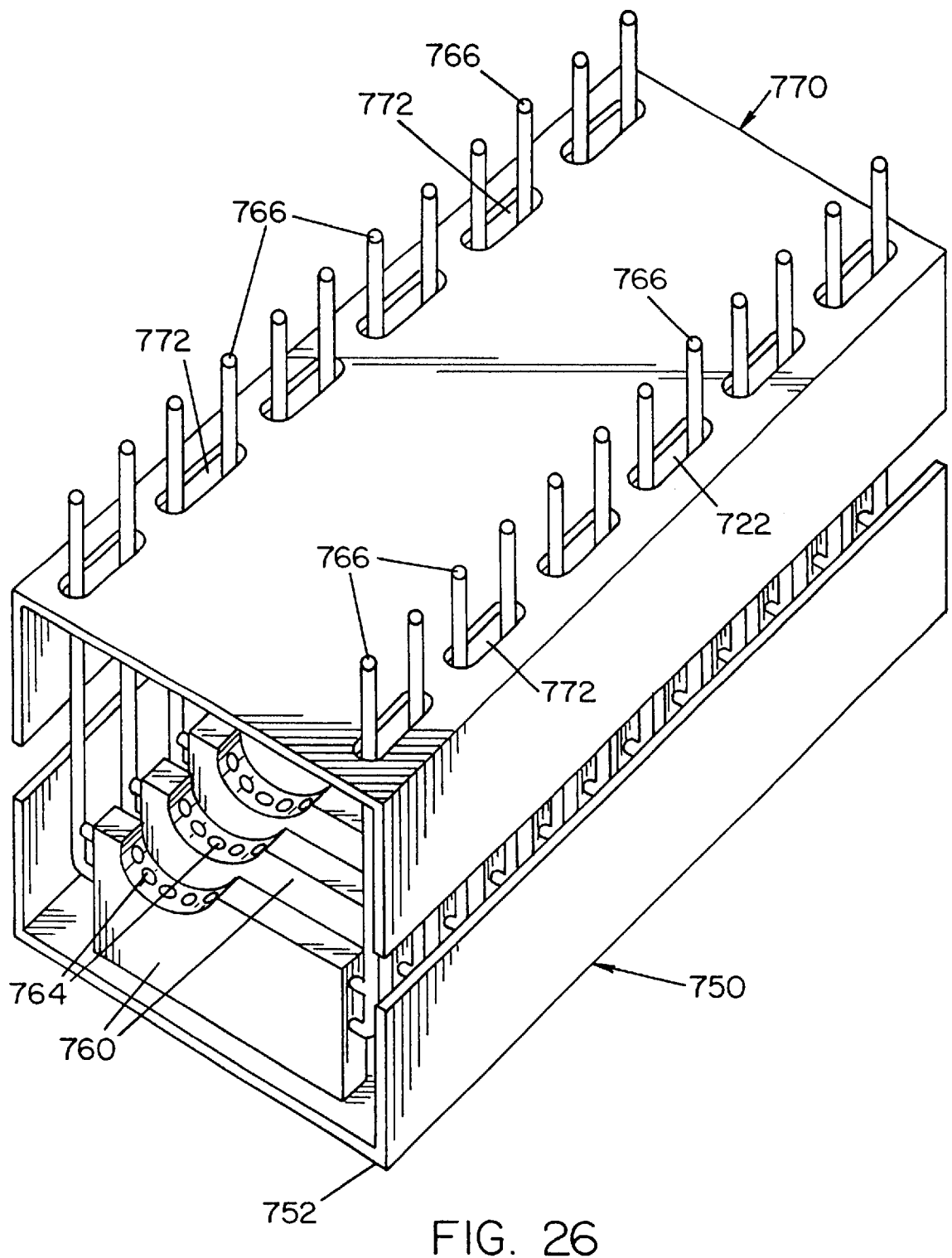
FIG. 26 is a pictorial view showing the quench station used in the preferred embodiment of the present invention.

The invention has been described with a simple shaped workpiece. In the preferred embodiment, the cylindrical workpiece is to be formed into a tubular structural component having an undulating profile in the axial direction. Thus, a preform step is needed to prepare the workpiece. This preform step is followed by a preheat and then hot metal gas forming in station 24. Consequently, a preform die 600, as shown in FIG. 22, is mounted by base 602 at station 22 of machine 20 as shown in FIGS. 2–4. This die has an elongated nest 610 with the desired profile to be imparted to the cylindrical workpiece preparatory to the forming operation. In this manner, the cylindrical sheet metal workpiece, which has been plugged, is preformed in nest 610. This forms the cylindrical workpiece so it will easily fit in the cavity of die set 60 for the subsequent forming operation. FIG. 23 illustrates lower die member 700 for the workpiece preformed by the die 600 in FIG. 22. This lower die member is matched with a similar upper die member for the gas forming operation. It includes shell 702, framework 704 and a large number of axially spaced conductors 710. These axially spaced conductors of the induction heating equipment are embedded within the ceramic fill material 720 of lower die 700. Conductors C are spaced along the shell a small distance less than 0.50 inches. FIG. 24 is a pictorial enlarged view of one end of lower die member 700 as shown in FIG. 23 with a shell 712 and opening 714. Fill material 720 is removed to illustrate the encircling, closely spaced conductors 710 supported in framework 704. For the preferred preformed workpiece processed by the die set shown in FIG. 22 and the lower die member shown in FIGS. 23 and 24, there is provided a quench unit 750 mounted at station 26 of machine 20. This quench unit is illustrated in FIGS. 5 and 26 as including a lower support base 752 having upstanding quench stands 760 and support stands 760a which may not be used for quenching. In quench stands 760, the heated formed workpiece is supported by nest 762 having quenching holes 764 directing quench liquid onto the heated workpiece from inlets 766. A cover 770 shown in FIG. 26 is positioned over base 752 during the quenching operation to allow proper quenching of the workpiece. Opening 772 provides clearance for quench inlets 766. Nest 762a in stands 760a merely support the heated workpiece during the quenching operation. However, they can be used for quenching of this area of the workpiece if needed. Quench stands 760 receive the desired amount of quenching liquid for the quench operation as discussed in connection with FIG. 19. By using selective quenching, together with selective heating, the forming operation is optimized. In addition, the metallurgical properties of the final formed structural component are optimized. In accordance with the invention, coils or conductors are closely spaced along the die members and quench stands are also closely spaced along quench unit 750. However, the amount of heating and the amount of quenching is controlled to give effective forming and desired properties of the finished product.

Figure 27:
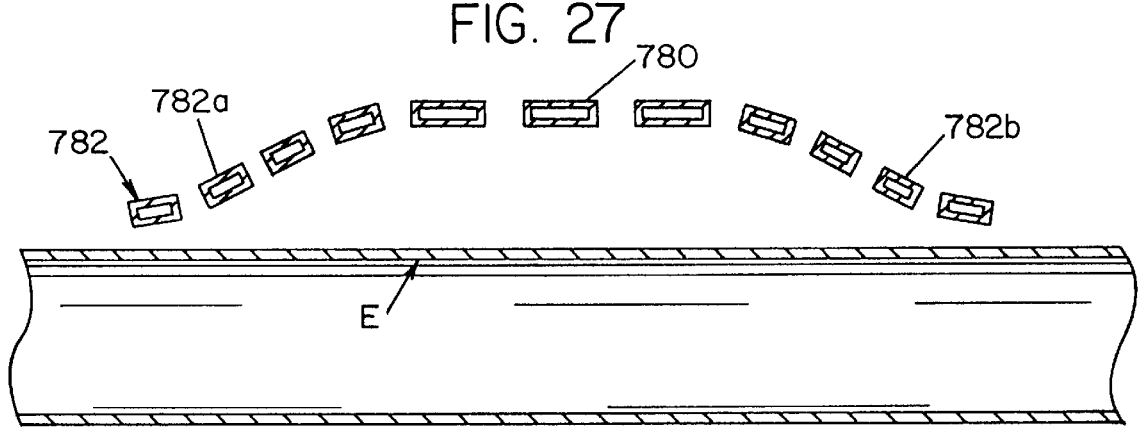
FIG. 27 is a cross sectional view showing two induction heating coils around the forming shell or cavity with the coils separated to provide distinct induction heating cycles during the forming of the tubular blank.
Figure 28A:
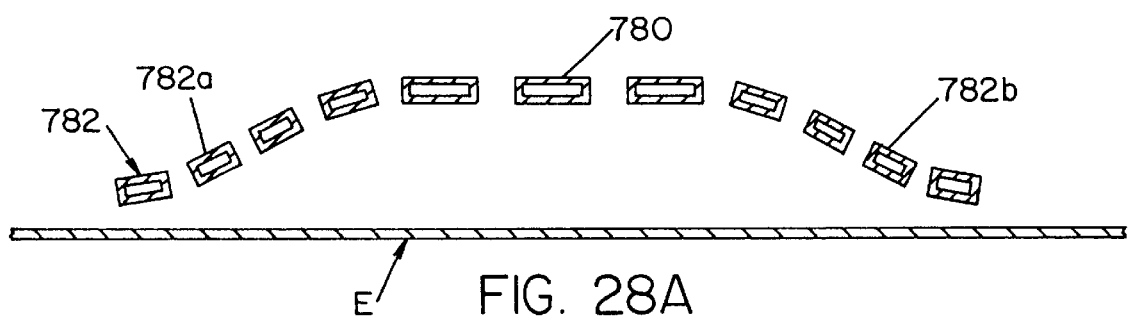
FIGS. 28A and 28B are views similar to FIG. 27 illustrating operating characteristics of the selectively controlled induction heating during the forming of the tubular blank; and, FIG. 29 is an end view of a cooling mechanism for causing arrested cooling of the heated workpiece after it has been formed.
Figure 28B:
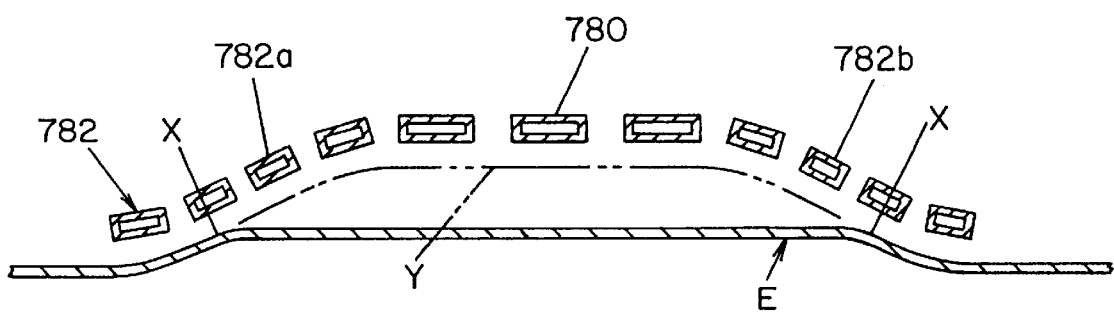

A further feature of the present invention is illustrated in FIGS. 27, 28A and 28B wherein a central multi-turn induction heating coil 780 surrounds the cavity into which the hollow workpiece illustrated as a single sheet E is to be formed by gas. A second induction heating coil 782 includes spaced sections 782a, 782b on opposite ends of central coil 780. A profile formed by coil sections 782a, 782b with coil 780 is the shape of the cavity 200 into which workpiece E is to be formed. Since coils 782a, 782b are close to workpiece E before it is formed, they heat the axially spaced sections X before the center portion Y of the workpiece is heated. Thus, the forming operation first causes movement of sheet E in area X, as shown in FIG. 28B. Thus, during the initial heating of the workpiece, which is a tube, the tube deforms first in areas adjacent the closer induction heating coil section 782a, 782b. If the heating operation were discontinued at that time, the invention would still have been performed in that the portions X were formed into the shape of the cavity 200. With continued heating and gas pressure, workpiece E eventually shifts into the full cavity 200, defined by the contour of the coils 780, 782, as shown in FIGS. 27, 28A and 28B. These schematic representations are used to illustrate that the induction heating affects the ease of forming the workpiece during the hot metal gas forming process. The closer the coils are to the metal constituting the workpiece E, the greater the heating effect. However, the heating equalizes as the workpiece assumes the final shape of the shell 200.

By providing controllable pressures for the inert gases, selective location or operation of the induction heating conductors along and at various positions around the shell, and selective, controlled quenching the forming process is controlled to avoid a necking and/or wrinkle condition. Coordination of these acts with controlled in-feeding of metal produces uniform end products. During the process, the induction heating at certain areas can be performed in die set 60 before final heating and forming. During the forming, the gas pressure can be modified, and in some examples is modified together with the induction heating being modified on a time basis. By selective heating and modified heating during the forming process the flow of metal is controlled. This is thermal enhanced intelligent forming. The invention is not restricted to heating of a workpiece to a given amount during gas forming at a fixed pressure.

The workpiece being formed by the invention is a hollow structure or blank formed from a thin (0.40–0.35 inches) electrically conductive material, preferably steel (for hardening) and aluminum. However, brass and titanium have been successfully formed. After the metal has been inductively heated by cycles where areas are heated selectively, at different times and different temperatures, the workpiece is selectively quenched at station 26 by liquid or air at controlled times and cycles. This quenching operation gives aluminum dimensional stability. The quenching operation is by a rapid quench cycle with liquid or gas or an arrested cooling quench as disclosed in U.S. Pat. No. 4,637,844, incorporated by reference herein. Combinations of rapid quenching and arrested cooling can be used at different portions of the inductively heated and formed workpiece. It has been found that some steels used for the automobile industry should be cooled at a slower rate to maintain their high strength whereas other steels are quenched to be hardened after heated for forming. Mist cooling, arrested cooling, and rapid quenching are selectively used to obtain the desired final metallurgical properties in all areas of the final product. This procedure is also used for various aluminum alloys formed in accordance with the invention.

Figure 29:
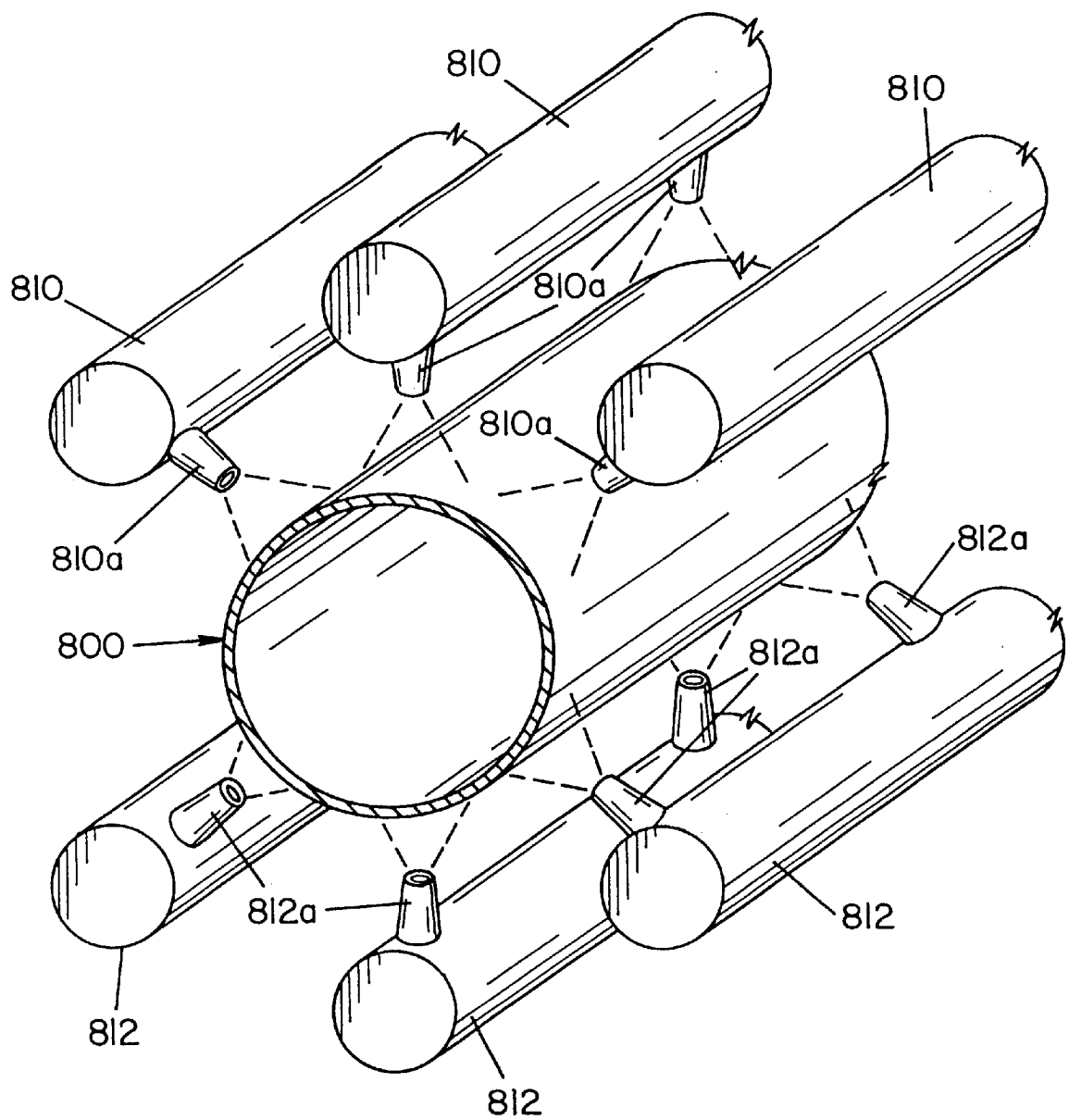

In some processes, arrested cooling is used wherein the workpiece is quenched to a given temperature and held at that temperature for a selected time. Such procedure is illustrated in FIG. 29 wherein workpiece 800 is surrounded by hot fluid manifolds 810 and 812 for directing fluid at a given temperature above ambient from nozzles 810a, 812a (only a few of which are shown). This action cools workpiece 800 to the temperature of the hot fluid where it is held until the fluid flow is stopped. This process can be used to obtain banite or to obtain other processing objectives.

The invention has been described in connection with either the preferred preformed workpiece or a non-preformed workpiece with a simple shape. The shape of the workpiece is not important. The various disclosed apparatus can be used interchangeably to form the desired hot metal gas formed hollow structural component of various workpiece shapes. The process involves a tubular metal workpiece which is plugged and subject to high gas pressure in the range of 200–1000 psi. During this process, the metal is heated by induction heating. In accordance with an aspect of the invention, the heating process is modulated along the length to accomplish the desired forming operation and desired heat distribution during the forming process. In accordance with a novel aspect, the heated workpiece is then quenched selectively along its length to create the desired metallurgical properties of the finished product. The induction heating while forming by inert gas followed by quenching of the final part is a novel method and obtains desired metallurgical properties. Other modifications can be made in the present invention without departing from the intended spirit and scope as defined in the accompanying claims.

Having thus defined the invention, the following is claimed:

1. A method of forming an elongated blank into a structural component having a predetermined outer configuration, said method comprising:

(a) providing a shape imparting shell formed from a low permeability, rigid material, said shell at least partially in the form of first and a second shell portions, each of which includes an inner surface defining said predetermined shape, an outer support and mounting surface and spaced lateral edges which edges define a parting plane between said two shell portions when said shell portions are brought together to at least partially form said shell;

(b) providing a first die member with an upper side and a lower side and having a support framework for carrying said first shell portion mounted in said framework by a first cast compression force transmitting material with said laterally spaced edges of said first shell portion facing outwardly from said lower side of said first die member, said first cast material having different physical properties from said rigid material of said first shell portion;

(c) providing a second die member with an upper side and a lower side and having a support framework for carrying said second shell portion mounted in said framework by a second cast compression force transmitting material with said laterally spaced edges of said second shell portion facing outwardly from said upper side of said second die member, said second cast material having different physical properties from said rigid material of said second shell portion, at least one of said first and second cast materials having a strength and hardness substantially less than said rigid material of at least one of said first and second shell portions;

(d) placing said blank into said second shell portion in said second die member;

(e) moving said first die member relative to said second die member to at least partially capture said blank in said shape imparting shell; and (f) forming said blank into said structural component by heating portions of said blank and forcing a fluid at a high pressure into said blank until said blank at least partially conforms to at least a portion of the inner surfaces of said first and second shell portions to form said structural component, said heating at least partially by induction heating.

2. The method as defined in claim 1, wherein said rigid material includes ceramic having a high hardness.

3. The method as defined in claim 2, wherein said rigid material includes fused silica impregnated with nitrogen.

4. The method as defined in claim 3, wherein said support framework includes machined metal.

5. The method as defined in claim 4, wherein said fluid is forced into said blank while said blank is heated.

6. The method as defined in claim 5, including the step of heating said blank before forming said blank.

7. The method as defined in claim 5, including sensing the pressure of said fluid in said shell and at least partially controlling the gas pressure of the gas forced into said blank to a preselected value.

8. The method as defined in claim 7, wherein said preselected value is about 200–1000 psi.

9. The method as defined in claim 4, wherein said predetermined shape has an axial profile and including the step of at least partially preforming said blank into an axial profile generally confirming to said axial profile of said predetermined shape.

10. The method as defined in claim 9, including the step of heating said blank before forming said blank.

11. The method as defined in claim 9, wherein said induction heating varied along a length of said blank to modulate the temperature/time pattern along said length.

12. The method as defined in claim 11, wherein said induction heating is at least partially varied by varying a frequency of an alternating current powering spaced conductors.

13. The method as defined in claim 11, wherein said induction heating is at least partially varied by varying a heating time of an alternating current powering said axially spaced conductors.

14. The method as defined in claim 11, wherein said induction heating is at least partially varied by varying the distance said axially spaced conductors are from at least one of said first and second shell portions.

15. The method as defined in claim 11, wherein said induction heating is at least partially varied by varying the spacing between said axially spaced conductors.

16. The method as defined in claim 11, wherein said induction heating is at least partially varied by varying the power of an alternating current powering said axially spaced conductors.

17. The method as defined in claim 11, wherein said induction heating is at least partially varied by varying the permeability of the flux field of selected spaced conductors.

18. The method as defined in claim 17, wherein said flux field is at least partially varied by a flux concentrator positioned along a length of said blank.

19. The method as defined in claim 17, wherein said flux field is at least partially varied by a Faraday shield positioned along said length of said blank.

20. The method as defined in claim 9, including transferring said formed structural component into a quench station and at least partially quenching said structural component at least partially along a length of said structural component.

21. The method as defined in claim 20, including at least partially varying said quenching at least partially along said length of said structural component.

22. The method as defined in claim 21, wherein said quench variation is by at least partially varying the flow rate of quenching fluid at least partially along said length of said structural component.

23. The method as defined in claim 21, wherein said quench variation is by at least partially changing location of said quenching operation at least partially along said length of said structural component.

24. The method as defined in claim 20, wherein said quenching cools said structural component to a given temperature above ambient for a time to provide arrested cooling.

25. The method as defined in claim 9, including sensing the pressure of said fluid in said shell and at least partially controlling the gas pressure of the gas forced into said blank to a preselected value.

26. The method as defined in claim 25, wherein said preselected value is about 200–1000 psi.

27. The method as defined in claim 2, wherein said rigid material includes a material selected from the group consisting of silicon nitride, silicon carbide, beryllium oxide, boron oxide, and zirconium.

28. The method as defined in claim 27, wherein said support framework includes machined metal.

29. The method as defined in claim 28, wherein said predetermined shape has an axial profile and including the step of at least partially preforming said blank into an axial profile generally confirming to said axial profile of said predetermined shape.

30. The method as defined in claim 29, including the step of heating said blank before forming said blank.

31. The method as defined in claim 29, wherein said induction heating varied along a length of said blank to modulate the temperature/time pattern along said length.

32. The method as defined in claim 31, wherein said induction heating is at least partially varied by varying a frequency of an alternating current powering spaced conductors.

33. The method as defined in claim 31, wherein said induction heating is at least partially varied by varying a heating time of an alternating current powering said axially spaced conductors.

34. The method as defined in claim 31, wherein said induction heating is at least partially varied by varying the distance said axially spaced conductors are from at least one of said first and second shell portions.

35. The method as defined in claim 31, wherein said induction heating is at least partially varied by varying the spacing between said axially spaced conductors.

36. The method as defined in claim 31, wherein said induction heating is at least partially varied by varying the power of an alternating current powering said axially spaced conductors.

37. The method as defined in claim 31, wherein said induction heating is at least partially varied by varying the permeability of the flux field of selected spaced conductors.

38. The method as defined in claim 37, wherein said flux field is at least partially varied by a flux concentrator positioned along a length of said blank.

39. The method as defined in claim 37, wherein said flux field is at least partially varied by a Faraday shield positioned along said length of said blank.

40. The method as defined in claim 29, including transferring said formed structural component into a quench station and at least partially quenching said structural component at least partially along a length of said structural component.

41. The method as defined in claim 40, including at least partially varying said quenching at least partially along said length of said structural component.

42. The method as defined in claim 41, wherein said quench variation is by at least partially varying the flow rate of quenching fluid at least partially along said length of said structural component.

43. The method as defined in claim 41, wherein said quench variation is by at least partially changing location of said quenching operation at least partially along said length of said structural component.

44. The method as defined in claim 40, wherein said quenching cools said structural component to a given temperature above ambient for a time to provide arrested cooling.

45. The method as defined in claim 29, including sensing the pressure of said fluid in said shell and at least partially controlling the gas pressure of the gas forced into said blank to a preselected value.

46. The method as defined in claim 45, wherein said preselected value is about 200–1000 psi.

47. The method as defined in claim 1, wherein said rigid material includes fused silica impregnated with nitrogen.

48. The method as defined in claim 1, wherein said rigid material includes a material selected from the group consisting of silicon nitride, silicon carbide, beryllium oxide, boron oxide, and zirconium.

49. The method as defined in claim 1, wherein said support framework includes machined metal.

50. The method as defined in claim 49, wherein said machined metal includes aluminum.

51. The method as defined in claim 1, wherein said fluid is forced into said blank prior to heating said blank.

52. The method as defined in claim 51, wherein said fluid is gas.

53. The method as defined in claim 51, including the step of heating said blank before forming said blank.

54. The method as defined in claim 51, including sensing the pressure of said fluid in said shell and at least partially controlling the gas pressure of the gas forced into said blank to a preselected value.

55. The method as defined in claim 54, wherein said preselected value is about 200–1000 psi.

56. The method as defined in claim 1, wherein said fluid is forced into said blank after said blank is heated.

57. The method as defined in claim 56, wherein said fluid is gas.

58. The method as defined in claim 56, including the step of heating said blank before forming said blank.

59. The method as defined in claim 56, including sensing the pressure of said fluid in said shell and at least partially controlling the gas pressure of the gas forced into said blank to a preselected value.

60. The method as defined in claim 59, wherein said preselected value is about 200–1000 psi.

61. The method as defined in claim 1, wherein said fluid is gas.

62. The method as defined in claim 5, wherein said fluid is gas.

63. The method as defined in claim 62, including transferring said formed structural component into a quench station and at least partially quenching said structural component at least partially along a length of said structural component.

64. The method as defined in claim 63, including at least partially varying said quenching at least partially along said length of said structural component.

65. The method as defined in claim 64, wherein said quench variation is by at least partially varying the flow rate of quenching fluid at least partially along said length of said structural component.

66. The method as defined in claim 64, wherein said quench variation is by at least partially changing location of said quenching operation at least partially along said length of said structural component.

67. The method as defined in claim 63, wherein said quenching cools said structural component to a given temperature above ambient for a time to provide arrested cooling.

68. The method as defined in claim 62, including sensing the pressure of said fluid in said shell and at least partially controlling the gas pressure of the gas forced into said blank to a preselected value.

69. The method as defined in claim 68, wherein said preselected value is about 200–1000 psi.

70. The method as defined in claim 1, wherein said blank has at least one opening.

71. The method as defined in claim 70, wherein said blank has at least two openings.

72. The method as defined in claim 71, wherein said blank is metal.

73. The method as defined in claim 1, wherein said blank is metal.

74. The method as defined in claim 1, wherein said predetermined shape has an axial profile and including the step of at least partially preforming said blank into an axial profile generally confirming to said axial profile of said predetermined shape.

75. The method as defined in claim 1, including the step of heating said blank before forming said blank.

76. The method as defined in claim 1, wherein said induction heating varied along a length of said blank to modulate the temperature/time pattern along said length.

77. The method as defined in claim 76, wherein said induction heating is at least partially varied by varying a frequency of an alternating current powering spaced conductors.

78. The method as defined in claim 76, wherein said induction heating is at least partially varied by varying a heating time of an alternating current powering said axially spaced conductors.

79. The method as defined in claim 76, wherein said induction heating is at least partially varied by varying the distance said axially spaced conductors are from at least one of said first and second shell portions.

80. The method as defined in claim 76, wherein said induction heating is at least partially varied by varying the spacing between said axially spaced conductors.

81. The method as defined in claim 76, wherein said induction heating is at least partially varied by varying the power of an alternating current powering said axially spaced conductors.

82. The method as defined in claim 76, wherein said induction heating is at least partially varied by varying the permeability of the flux field of selected spaced conductors.

83. The method as defined in claim 82, wherein said flux field is at least partially varied by a flux concentrator positioned along a length of said blank.

84. The method as defined in claim 82, wherein said flux field is at least partially varied by a Faraday shield positioned along said length of said blank.

85. The method as defined in claim 1, wherein said heating is at least partially by passing a heating current through said blank.

86. The method as defined in claim 85, including transferring said formed structural component into a quench station and at least partially quenching said structural component at least partially along a length of said structural component.

87. The method as defined in claim 86, including at least partially varying said quenching at least partially along said length of said structural component.

88. The method as defined in claim 87, wherein said quench variation is by at least partially varying the flow rate of quenching fluid at least partially along said length of said structural component.

89. The method as defined in claim 87, wherein said quench variation is by at least partially changing location of said quenching operation at least partially along said length of said structural component.

90. The method as defined in claim 86, wherein said quenching cools said structural component to a given temperature above ambient for a time to provide arrested cooling.

91. The method as defined in claim 85, including sensing the pressure of said fluid in said shell and at least partially controlling the gas pressure of the gas forced into said blank to a preselected value.

92. The method as defined in claim 91, wherein said preselected value is about 200–1000 psi.

93. The method as defined in claim 1, including transferring said formed structural component into a quench station and at least partially quenching said structural component at least partially along a length of said structural component.

94. The method as defined in claim 93, including at least partially varying said quenching at least partially along said length of said structural component.

95. The method as defined in claim 94, wherein said quench variation is by at least partially varying the flow rate of quenching fluid at least partially along said length of said structural component.

96. The method as defined in claim 94, wherein said quench variation is by at least partially changing location of said quenching operation at least partially along said length of said structural component.

97. The method as defined in claim 93, wherein said quenching cools said structural component to a given temperature above ambient for a time to provide arrested cooling.

98. The method as defined in claim 1, including sensing the pressure of said fluid in said shell and at least partially controlling the gas pressure of the gas forced into said blank to a preselected value.

99. The method as defined in claim 98, wherein said preselected value is about 200–1000 psi.

100. The method as defined in claim 1, including feeding of said blank into said shell while said blank is being formed.

101. A method of forming an elongated metal blank with a length between first and second ends, at least one of said ends being open, into a structural component having a predetermined outer configuration, said method comprising:
  (a) placing said metal blank into a cavity of a shell which cavity has an inner surface surrounding said metal blank, said shell at least partially supported in a cast non-magnetic material, said shell formed from a low permeability, rigid material, said low permeability, rigid material of said shell having different physical properties from said supporting cast non-magnetic material, said supporting cast non-magnetic material has a strength and hardness that is different from said low permeability, rigid material of said shell; and,
  (b) forming said metal blank into said structural component by heating axial portions along the length of said metal blank by at least one heating element positioned adjacent said shell while forcing fluid at a high pressure into said metal blank until said metal blank conforms to at least a portion of said inner surface of said cavity to form said structural component.

102. The method as defined in claim 101, wherein said supporting cast non-magnetic material has a strength and hardness that is different from said low permeability, rigid material of said shell.

103. The method as defined in claim 101, wherein said supporting cast non-magnetic material has a strength and hardness substantially less than said low permeability, rigid material of said shell.

104. The method as defined in claim 103, wherein said low permeability, rigid material includes ceramic having a high hardness.

105. The method as defined in claim 103, wherein said low permeability, rigid material includes fused silica.

106. The method as defined in claim 103, wherein said low permeability, rigid material includes a material selected from the class consisting of silicon nitride, silicon carbide, beryllium oxide, boron oxide, and zirconium.

107. The method as defined in claim 101, wherein said metal blank has two open ends.

108. The method as defined in claim 101, including preheating said metal blank before forming said metal blank.

109. The method as defined in claim 108, wherein said preheating is by passing a heating current through said metal blank.

110. The method as defined in claim 109, wherein said heating current is an AC current.

111. The method as defined in claim 101, wherein said heating element includes induction heating conductors that are axially spaced along the length of said metal blank.

112. The method as defined in claim 111, including transferring said formed structural component into a quench station and quenching said structural component along the axial length of said structural component.

113. The method as defined in claim 112, including varying said quenching along said axial length.

114. The method as defined in claim 113, wherein said quench variation is by varying the flow rate of quenching fluid along said length.

115. The method as defined in claim 114, wherein said quench variation is by changing location of said quenching operation along said length.

116. The method as defined in claim 101, wherein said induction heating is varied along the length of said metal blank to modulate the temperature/time pattern along said length.

117. The method as defined in claim 116, wherein said varied indiction heating is by varying the frequency of an alternating current powering said axially spaced conductors.

118. The method as defined in claim 116, wherein said varied indiction heating is by varying the distance between said axially spaced conductors.

119. The method as defined in claim 116, wherein said varied indiction heating is by varying the spacing between said axially spaced conductors.

120. The method as defined in claim 116, wherein said varied indiction heating is by varying the power of an alternating current powering said axially spaced conductors.

121. The method as defined in claim 116, wherein said varied indiction heating is by varying the heating time of an alternating current powering said axially spaced conductors.

122. The method as defined in claim 116, wherein said varied indiction heating is by varying the permeability of the flux field of selected spaced conductors.

123. The method as defined in claim 122, wherein said flux field is varied by a flux concentrator positioned along the length of said metal blank.

124. The method as defined in claim 122, wherein said flux field is varied by a Faraday shield positioned along said length of said metal blank.

125. The method as defined in claim 101, including transferring said formed structural component into a quench station and quenching said structural component along the axial length of said structural component.

126. The method as defined in claim 125, including varying said quenching along said axial length.

127. The method as defined in claim 126, wherein said quench variation is by varying the flow rate of quenching fluid along said length.

128. The method as defined in claim 126, wherein said quench variation is by changing location of said quenching operation along said length.

129. The method as defined in claim 125, wherein said quenching cools said structural component to a given temperature above ambient for a time to provide arrested cooling.

130. The method as defined in claim 101, including sensing the pressure of a gas in said shell and controlling the gas pressure of the gas forced into said metal blank to a preselected value.

131. The method as defined in claim 130, wherein said preselected value is in the range of about 200–1000 psi.

* * * * *

Disclaimer 6,613,164—William C. Dykstra, Rockford, MI; George D. Pfaffmann, Farmington Hills, MI; Xin Nmn Wu, Detroit, MI. METHOD OF FORMING A TUBULAR BLANK INTO A STRUCTURAL COMPONENT AND DIE THEREFOR. Patent dated September 2, 2003. Disclaimer filed October 17, 2003, by the assignee, Hot Metal Gas Forming Intellectual Property, Inc.

The term of this patent, subsequent to the term of patent number, 6,322,645 has been disclaimed.

*(Official Gazette, March 2, 2004)*